United States Patent
Choi et al.

(10) Patent No.: US 10,639,006 B2
(45) Date of Patent: May 5, 2020

(54) FOCUSED ULTRASOUND OPERATION APPARATUS

(71) Applicant: HIRONIC CO., LTD., Seongnam-si, Gyeonggi-do (KR)

(72) Inventors: Moon Seok Choi, Yongin-si (KR); Seon Tai Kim, Seoul (KR); Sung Won Lee, Yongin-si (KR); Jin Woo Lee, Seongnam-si (KR); Jun Hyung Lee, Yongin-si (KR); Sang Hyeon Hwang, Seoul (KR); Tae Yun Kwon, Yongin-si (KR)

(73) Assignee: HIRONIC CO., LTD., Seongnam-si (KR)

( * ) Notice: Subject to any disclaimer, the term of this patent is extended or adjusted under 35 U.S.C. 154(b) by 431 days.

(21) Appl. No.: 15/537,219

(22) PCT Filed: Sep. 2, 2015

(86) PCT No.: PCT/KR2015/009224
§ 371 (c)(1),
(2) Date: Jun. 16, 2017

(87) PCT Pub. No.: WO2016/098995
PCT Pub. Date: Jun. 23, 2016

(65) Prior Publication Data
US 2018/0055478 A1    Mar. 1, 2018

(30) Foreign Application Priority Data

Dec. 19, 2014   (KR) .......................... 10-2014-0184725
Dec. 29, 2014   (KR) .......................... 10-2014-0192640
Jun. 1, 2015    (KR) .......................... 10-2015-0077629

(51) Int. Cl.
*A61B 8/12*   (2006.01)
*A61N 7/02*   (2006.01)
(Continued)

(52) U.S. Cl.
CPC .................. *A61B 8/12* (2013.01); *A61B 8/46* (2013.01); *A61B 18/04* (2013.01); *A61N 7/02* (2013.01);
(Continued)

(58) Field of Classification Search
CPC ............. A61N 7/00; A61N 7/02; A61N 7/022
See application file for complete search history.

(56) References Cited

U.S. PATENT DOCUMENTS 5,720,287 A * 2/1998 Chapelon ................. A61B 8/12
600/439
5,762,066 A * 6/1998 Law ........................ A61B 8/06
600/439

(Continued)

FOREIGN PATENT DOCUMENTS

JP     2006-523129 A    10/2006
KR  10-2011-0020293 A    3/2011

(Continued)

OTHER PUBLICATIONS

Partial Supplementary European search report dated Dec. 14, 2017 from the corresponding Application No. EP 15870163.1, 16 pp.

(Continued)

*Primary Examiner* — Carolyn A Pehlke
(74) *Attorney, Agent, or Firm* — Brinks Gilson & Lione

(57) ABSTRACT

Disclosed is a focused ultrasound operation apparatus that includes: an operation hand piece that includes a handle unit that is used as a handle for a user; a cartridge that includes an ultrasound treatment unit, which generates a focused ultrasound, and has the shape of a circular cylinder or bar, the cartridge being attached to, and detached from, the operation hand piece; a window provided on the cartridge to pass the focused ultrasound generated by the ultrasound treatment unit; and a driver that drives the ultrasound (Continued)

treatment unit to move the ultrasound treatment unit forward and backward.

12 Claims, 19 Drawing Sheets

(51) Int. Cl.
*A61B 8/00* (2006.01)
*A61B 18/04* (2006.01)
*A61N 7/00* (2006.01)
*A61B 90/00* (2016.01)
*A61B 8/08* (2006.01)
*A61B 18/00* (2006.01)

(52) U.S. Cl.
CPC ............ *A61N 7/022* (2013.01); *A61B 8/0858* (2013.01); *A61B 2018/00559* (2013.01); *A61B 2018/00636* (2013.01); *A61B 2090/062* (2016.02); *A61B 2090/065* (2016.02); *A61N 2007/0034* (2013.01); *A61N 2007/0043* (2013.01); *A61N 2007/0052* (2013.01); *A61N 2007/0082* (2013.01); *A61N 2007/0091* (2013.01)

(56) References Cited

U.S. PATENT DOCUMENTS

| 7,052,462 | B2 | 5/2006 | Fukuda et al. |
| 2004/0204650 | A1 | 10/2004 | Taylor |
| 2007/0219602 | A1* | 9/2007 | Ostrovsky .............. A61N 7/022 607/96 |
| 2012/0016239 | A1* | 1/2012 | Barthe ................. A61B 8/0858 600/439 |
| 2012/0046547 | A1 | 2/2012 | Barthe et al. |
| 2013/0178738 | A1 | 7/2013 | Martin et al. |

FOREIGN PATENT DOCUMENTS

| KR | 10-2011-0032122 A | 3/2011 |
| KR | 10-2012-0100049 A | 9/2012 |
| KR | 10-1335476 B | 12/2013 |
| KR | 10-1372494 B1 | 3/2014 |
| KR | 10-2014-0055870 A | 5/2014 |
| WO | 2011/034986 A2 | 3/2011 |

OTHER PUBLICATIONS

International Search Report dated Sep. 12, 2016, corresponding to PCT/KR2015/009224 (4 Pages).

* cited by examiner

FIG. 2
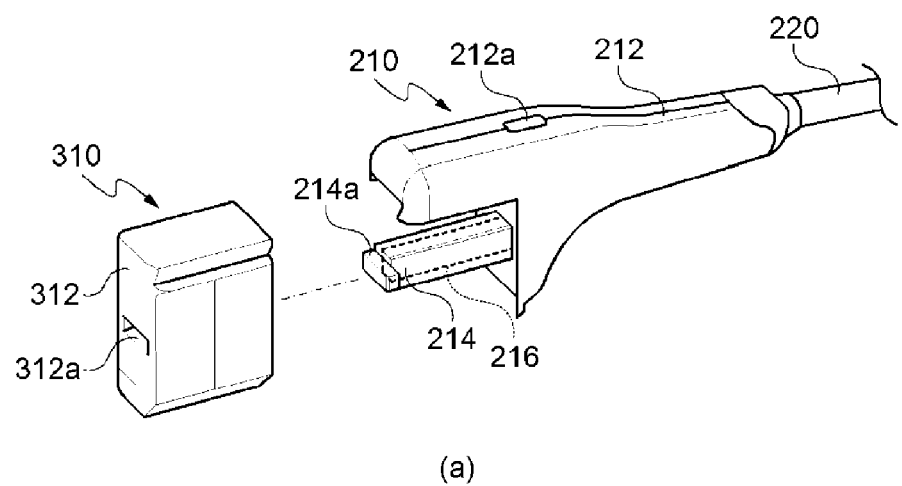
(a)
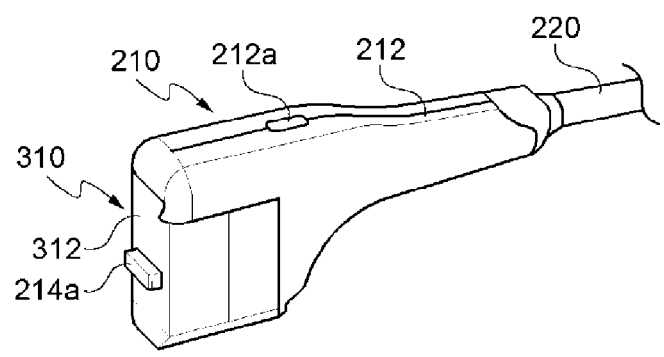
(b)

FOCUSED ULTRASOUND OPERATION APPARATUS

CROSS-REFERENCE TO RELATED APPLICATIONS

This application is a filing under 35 U.S.C. § 371 of International Patent Application PCT/KR2015/009224 filed Sep. 2, 2015, and claims priority to and the benefit of KR 10-2014-0184725 filed Dec. 19, 2014; 10-2014-0192640 filed Dec. 29, 2014; and 10-2015-0077629 filed Jun. 1, 2015. These applications are incorporated by reference herein in their entirety.

FIELD

The present disclosure relates to a focused ultrasound operation apparatus, and more particularly, to a focused ultrasound operation apparatus capable of improving efficiency of gynecological disease treatment and/or vaginal tightening operation.

BACKGROUND

The statements in this section merely provide background information related to the present disclosure and may not constitute prior art.

Nowadays, an interest in skin care and obesity treatment is increasing day by day, and accordingly, various medical devices for skin care and obesity treatment are being developed. For example, various skin care medical devices for patients who wish to receive face lifting or skin tightening operation are being developed, and on the other hand, medical device for obesity treatment are being developed.

As skin care medical devices, there are medical devices using an invasive method in which skin tissue is cut. However, as an operation safety problem, a patient's feeling of rejection, etc. are coming to the fore, medical devices using a non-invasive method in which operation is possible without cutting skin tissue are gaining attention. Such a tendency is also exhibited similarly in fields of skin care, obesity treatment, etc., and the trend is expected to be exhibited also in other medical fields.

In keeping with this trend, as non-invasive medical devices, ultrasound medical devices that use high intensity focused ultrasound (HIFU) are coming into the spotlight nowadays. For example, there is an ultrasound medical device which non-invasively performs skin lifting or skin tightening operation by irradiating an inside of skin tissue with HIFU for skin care operation, and there is an ultrasound medical device which non-invasively burns or melts away adipose tissue to break down the adipose tissue by irradiating subcutaneous fat with HIFU for obesity treatment.

Meanwhile, patients with gynecological disease are steadily increasing nowadays. Generally, gynecological disease can be mainly classified as neoplastic disease, inflammatory disease, menstrual disorder, venereal disease, and sexual dysfunction. More specifically, typical tumors include cervical cancer and ovarian cancer, and neoplastic disease includes uterine myoma. Inflammatory disease includes leukorrhea, and menstrual disorder includes amenorrhea, menstrual pain, an abnormal menstrual cycle, and the like. Also, sexual dysfunction includes sexual desire disorder, sexual arousal disorder, orgasm disorder, pain disorder, vaginal contraction disorder, and the like. Among these, sexual dysfunction refers to a symptom of not obtaining or having difficulty obtaining satisfaction through sexual activity. Conventionally, female sexual dysfunction has been a natural disorder due to parturition or aging in many cases. However, nowadays, patients with sexual dysfunction are steadily increasing even among young people in their 20's and 30's. Although this phenomenon may have various causes, excessive smoking, drinking, drug abuse, stress, etc. are known as main causes of the increase in sexual dysfunction among young people.

Methods for treating such gynecological diseases may be mainly divided into treatment using medication and treatment using a medical device. Of these, the treatment using a medical device refers to treatment using a thermal treatment device, a wormwood moxibustion device, a sitz bath device, a laser treatment device, and the like. However, treatment using a thermal treatment device, a wormwood moxibustion device, or a sitz bath device is not direct treatment, and the effect thereof is also known as being very insignificant. Also, in the case of treatment using a laser treatment device, strong pain and bleeding occurs during operation, and great inconvenience to daily life is caused because pain and side effects occur even after operation.

Documents related to this include US2007-0232913 A1, KR2011-0091831 A1, KR2007-0065332 A1, KR2012-0116908 A1, KR2011-0121701 A1, and so on.

SUMMARY

It is an aspect of the present disclosure to provide a focused ultrasound operation apparatus with improved reliability.

It is another aspect of the present disclosure to provide a focused ultrasound operation apparatus by which ultrasound can be more stably transmitted.

Further, it is still another aspect of the present invention to provide a focused ultrasound operation apparatus capable of improving safety of gynecological disease treatment and/or vaginal tightening operation.

According to an embodiment of the present disclosure, a focused ultrasound operation apparatus includes an operation handpiece that is used as an operator's handle; a cartridge that is insertable into vagina of an operation target, is disposed to be attachable to and detachable from the operation handpiece, and has an ultrasound treatment part configured to generate focused ultrasound disposed therein; a driving device configured to drive the ultrasound treatment part so that the ultrasound treatment part moves back and forth along a longitudinal direction of the cartridge; a sensing device configured to determine whether the cartridge is normally placed inside the vagina; and a determination part configured to review sensed data sent from the sensing device and determine whether the cartridge is normally placed inside the vagina.

Here, the sensing device may include a first sensor arranged at one side of the cartridge to sense contact with a first position in the vagina; and a second sensor arranged at the other side of the cartridge to sense contact with a second position in the vagina which is different from the first position, wherein the determination part determines that the cartridge is normally placed when both the first sensor and the second sensor are sensed as being in contact with a skin surface inside the vagina and determines that the cartridge is abnormally placed when any of the first sensor and the second sensor is not sensed as being in contact with the skin surface inside the vagina.

The cartridge may include a bar-shaped cartridge body; and a window provided at a circumference of the cartridge body in the longitudinal direction of the cartridge so that focused ultrasound generated from the ultrasound treatment part is transmitted to the outside, the sensing device may include a first sensor arranged at one side of the window to sense contact with the first position in the vagina; and a second sensor arranged at the other side of the window to sense contact with the second position in the vagina which is different from the first position, and the determination part may determine that the cartridge is normally placed when both the first sensor and the second sensor are sensed as being in contact with a skin surface inside the vagina and determine that the cartridge is abnormally placed when any of the first sensor and the second sensor is not sensed as being in contact with the skin surface inside the vagina.

The sensing device may include a first sensor arranged at one side of the cartridge to sense contact with the first position inside the vagina; and a second sensor arranged at the other side of the cartridge to sense contact with the second position inside the vagina which is different from the first position, wherein the first sensor and the second sensor may be arranged on the same straight line crossing the longitudinal direction of the cartridge.

The sensing device may include third sensors arranged to be spaced apart from each other along the longitudinal direction of the cartridge, and the determination part may receive sensed data from the third sensors and calculate a depth by which the cartridge is inserted into the vagina during operation.

The focused ultrasound operation apparatus may further include an imaging probe configured to image skin tissue at a predetermined depth from a skin surface of the vagina; and a controller configured to analyze imaged data received from the imaging probe and control irradiation conditions of the focused ultrasound, and the cartridge may include a cartridge body that is disposed to be attachable to and detachable from the operation handpiece and has a cylindrical shape to be insertable into the vagina; a window coupled to the cartridge body to transmit the focused ultrasound and having a skin contact surface formed in a flat shape; and a buffering part formed of a flexible material having lower hardness than that of the cartridge body and provided as a part of the cartridge body, wherein the imaging probe may image a thickness of muscle of the vagina, and the controller may control irradiation conditions of the focused ultrasound of the ultrasound treatment part in consideration of the thickness of muscle of the vagina measured by the imaging probe.

According to an embodiment of the present invention, a focused ultrasound operation apparatus includes an operation handpiece that is used as an operator's handle; a cartridge that is insertable into vagina of an operation target, is disposed to be attachable to and detachable from the operation handpiece, and has an ultrasound treatment part configured to generate focused ultrasound disposed therein; a driving device configured to drive the ultrasound treatment part so that the ultrasound treatment part moves back and forth along a longitudinal direction of the cartridge; an imaging probe configured to image skin tissue at a predetermined depth from a skin surface of the vagina; and a controller configured to analyze imaged data received from the imaging probe and control irradiation conditions of the focused ultrasound.

Here, the imaging probe may image skin tissue at a depth in the range of 0.5 mm to 3.0 mm from a surface of the vagina, and the controller may control irradiation conditions of the focused ultrasound of the ultrasound treatment part in consideration of the skin tissue measured by the imaging probe.

The imaging probe may image a thickness of muscle of the vagina, and the controller may control irradiation conditions of the focused ultrasound of the ultrasound treatment part in consideration of the thickness of muscle of the vagina measured by the imaging probe.

The imaging probe may be coupled to the ultrasound treatment part and move back and forth together with the ultrasound treatment part.

The cartridge may include a bar-shaped cartridge body; and a window provided at a circumference of the cartridge body in the longitudinal direction of the cartridge so that focused ultrasound generated from the ultrasound treatment part is transmitted to the outside, wherein the imaging probe may image the thickness of muscle of the vagina by irradiating the vagina with ultrasound through the window.

The operation handpiece may include a cartridge rotating part configured to rotate the cartridge about a central axis of the cartridge, the cartridge rotating part may be coupled to the cartridge to rotate together with the cartridge, and the operation handpiece may include a fixing part to which the cartridge rotating part is rotatably coupled.

The controller may compare imaged data measured by the imaging probe with preset reference data, and when the thickness of muscle of the vagina is deviated from a preset thickness of vagina, may control the ultrasound treatment part so that irradiation of the focused ultrasound from the ultrasound treatment part is prevented.

The controller may compare imaging data measured by the imaging probe with preset reference data and control an irradiation depth of the focused ultrasound of the ultrasound treatment part so that a thermal focal point that is formed of the focused ultrasound is formed within a vertical width of the thickness of muscle of the vagina.

According to an embodiment of the present invention, a focused ultrasound operation apparatus includes an operation handpiece including a handle part that is used as an operator's handle; a cartridge having one side connected to the operation handle and an ultrasound treatment part configured to generate focused ultrasound disposed therein; and a driving device configured to drive the ultrasound treatment part, wherein the cartridge may include a cartridge body that is disposed to be attachable to and detachable from the operation handpiece and has a cylindrical shape to be insertable into vagina of an operation target; a window coupled to the cartridge body to transmit the focused ultrasound; and a buffering part formed of a flexible material having lower hardness than that of the cartridge body and provided as a part of the cartridge body.

Here, the buffering part may be formed of a material having elasticity.

Further, a skin contact surface of the window may be formed in a flat shape.

Further, the buffering part may have a relatively low elastic coefficient compared to that of the cartridge body.

According to an embodiment of the present invention, a focused ultrasound operation apparatus includes an operation handpiece including a handle part that is used as an operator's handle; a cartridge having an ultrasound treatment part configured to generate high intensity focused ultrasound (HIFU) disposed therein; and a driving device configured to drive the ultrasound treatment part, wherein the cartridge may include a cartridge body that is disposed to be attachable to and detachable from the operation handpiece and has a cylindrical shape to be insertable into vagina of an operation target; and a window coupled to a side surface of the cartridge body and provided to transmit the HIFU, and a skin contact surface of the HIFU window may have a flat surface.

Here, the cartridge body may include a protruding part that is formed to protrude in a direction perpendicular to the longitudinal direction of the cartridge body from the side surface of the cartridge body and has the HIFU window coupled thereto.

Further, a surface including a boundary line between the protruding part and the cartridge body may be a curved surface, and a surface including a line of contact between the protruding part and the HIFU window may be a flat surface.

According to an embodiment of the present invention, in a focused ultrasound operation apparatus, at least one of operation safety, apparatus reliability, and apparatus service life can be improved.

By comparing imaged data of skin tissue inside vagina on which a thermal focal point is attempted to be formed during operation with reference data and changing focused ultrasound operation conditions into suitable operation conditions, a focused ultrasound operation apparatus according to the present invention can improve safety of gynecological disease treatment and/or vaginal tightening operation.

By determining whether a cartridge inserted inside vagina during operation is normally placed inside the vagina and then performing operation to allow skin tissue with preset thermal focal points to be precisely irradiated with focused ultrasound, a focused ultrasound operation apparatus according to the present invention can improve safety of gynecological disease treatment and/or vaginal tightening operation.

Due to having cartridges which have operation conditions suitable for an operation target's state and are compatible to an operation handpiece and then being able to perform operation by installing a selected cartridge in the operation handpiece, a focused ultrasound operation apparatus according to an embodiment of the present invention can perform patient-tailored operation using single piece of equipment by replacing a cartridge.

By comparing imaged data of skin tissue inside vagina on which a thermal focal point is attempted to be formed during operation with reference data and changing focused ultrasound operation conditions into suitable operation conditions, a focused ultrasound operation method according to the present invention can improve safety of gynecological disease treatment and/or vaginal tightening operation.

By determining whether a cartridge inserted inside vagina during operation is normally placed inside the vagina and then performing operation to allow skin tissue with preset thermal focal points to be precisely irradiated with focused ultrasound, a focused ultrasound operation method according to the present invention can improve safety of gynecological disease treatment and/or vaginal tightening operation.

Due to having cartridges which have operation conditions suitable for an operation target's state and are compatible to an operation handpiece and then being able to perform operation by installing a selected cartridge in the operation handpiece, a focused ultrasound operation method according to an embodiment of the present invention can perform patient-tailored operation using single piece of equipment by replacing a cartridge.

DRAWINGS

In order that the disclosure may be well understood, there will now be described various forms thereof, given by way of example, reference being made to the accompanying drawings, in which:

FIG. 2 is a view for describing a coupling process between a first operation handle and a first cartridge illustrated in FIG. 1.

DETAILED DESCRIPTION

Hereinafter, a focused ultrasound operation apparatus and an operation method thereof according to an embodiment of the present disclosure will be described in detail with reference to the accompanying drawings.

Figure 1:
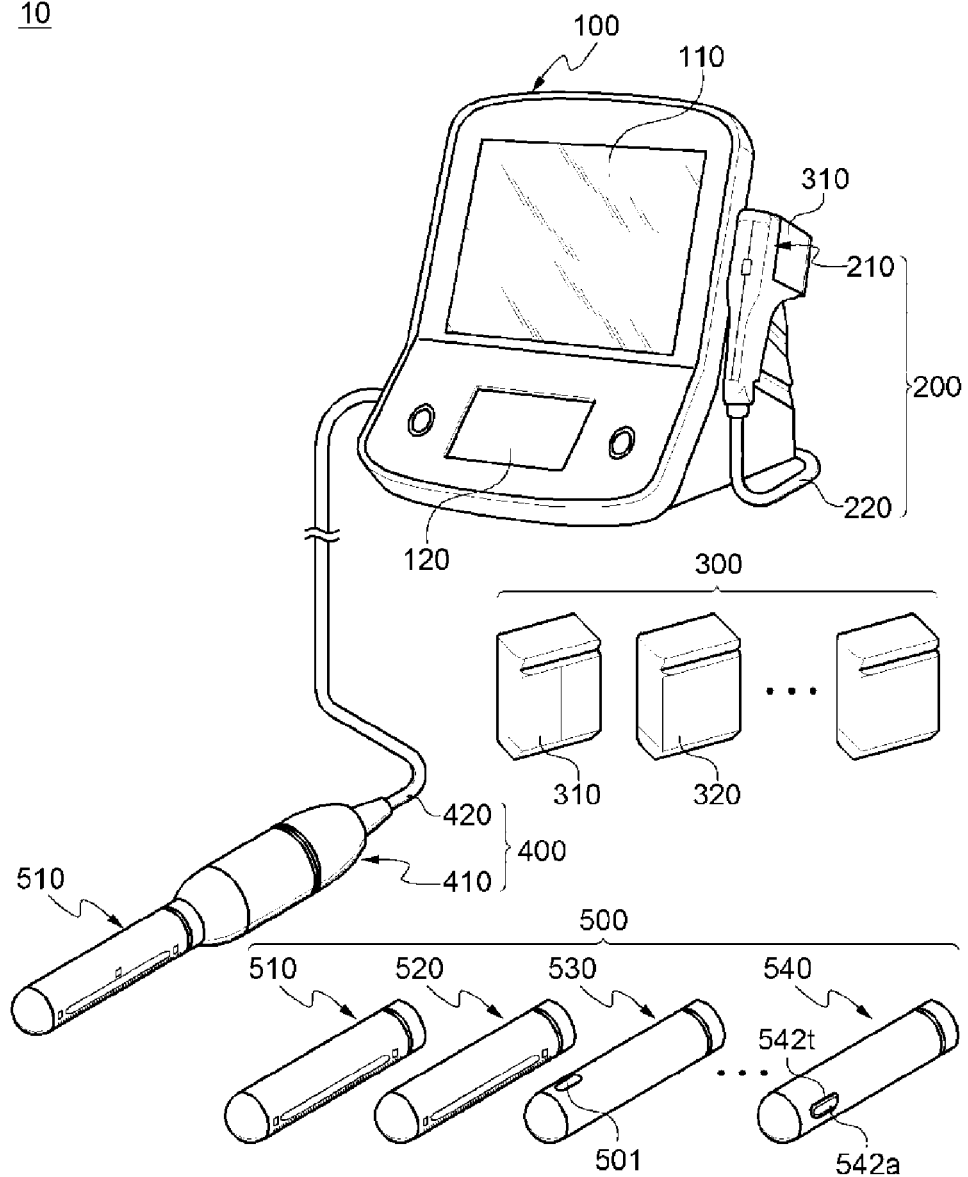
FIG. 1 is a perspective view schematically a focused ultrasound operation apparatus according to an embodiment of the present invention.
Figure 3:
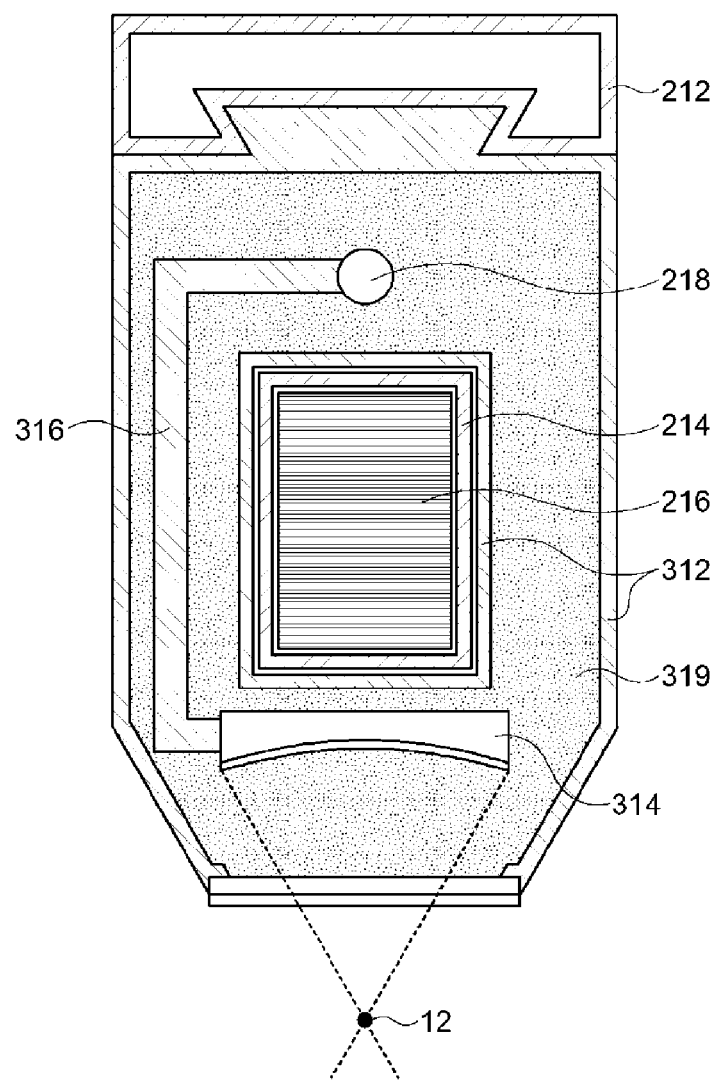
FIG. 3 is a cross-sectional view schematically illustrating the first operation handle and the first cartridge illustrated in FIG. 1.

FIG. 1 is a perspective view schematically a focused ultrasound operation apparatus according to an embodiment of the present invention, FIG. 2 is a view for describing a coupling process between a first operation handle and a first cartridge illustrated in FIG. 1, and FIG. 3 is a cross-sectional view schematically illustrating the first operation handle and the first cartridge illustrated in FIG. 1.

Referring to FIGS. 1 to 3, a focused ultrasound operation apparatus 10 according to an embodiment of the present invention may be a medical device capable of performing two or more different types of operations by using focused ultrasound.

Here, the two or more types of operations may include non-invasive face lifting or skin tightening operation, non-invasive operation for reducing or removing subcutaneous fat, and gynecological disease treatment and/or vaginal tightening operation.

The focused ultrasound may be for focusing ultrasound waves to be gathered at one focal point. For example, as one form of focused ultrasound, high intensity focused ultrasound (hereinafter referred to as "HIFU") may be for focusing ultrasound waves so that the ultrasound waves are gathered at one focal point with high intensity to form a thermal focal point 12. Alternatively, as another form of focused ultrasound, low intensity focused ultrasound (LIFU) may be for focusing ultrasound waves so that the ultrasound waves are gathered at one focal point with low intensity to form the thermal focal point 12. The thermal focal point 12 is a thermal focal point in a high-temperature state of about 60° C. or higher, and effects such as thermal effect and cavitation effect may occur at the thermal focal point 12.

The focused ultrasound operation apparatus 10 may perform face lifting or skin tightening operation by forming the thermal focal point 12 on dermis, fascia, or superficial musculoaponeurotic system (SMAS) layer which is placed at about 1.5 mm to 4.5 mm from skin surface or perform operation for reducing or removing fat by forming the thermal focal point 12 on subcutaneous fat which is placed at about 6.0 mm to 15.0 mm from skin surface. Alternatively, by forming a thermal focal point 22 (see FIG. 18) on skin tissue at a predetermined depth from a surface of a woman's vagina or muscle responsible for vaginal contraction, e.g., endopelvic fascia (EPF) 70 (see FIG. 18), the focused ultrasound operation apparatus 10 may perform operation of regenerating or restoring the EPF 70.

The focused ultrasound operation apparatus 10 may include an equipment main body 100, a first handpiece assembly 200, a first cartridge set 300, a second handpiece assembly 400, a second cartridge set 500, etc.

The equipment main body 100 may provide an operator (not illustrated) with operation-related information and may be used by the operator to operate or manipulate the focused ultrasound operation apparatus 10. For example, the equipment main body 100 may include a display 110 configured to display operation-related information for the operator and a manipulation part 120 configured to allow the operator to operate or control the focused ultrasound operation apparatus 10. A touchscreen or the like may be used as the manipulation part 120.

The first handpiece assembly 200 may include a first operation handpiece 210 and a first connecting cable 220. The first operation handpiece 210 is for irradiating an operation target with focused ultrasound and may be provided in a hand-held form to improve convenience of user manipulation. For example, the first operation handpiece 210 may include a first handle part 212 so that the operator can hold the first operation handpiece 210. A first operation switch 212a configured to allow the operator to control ultrasound irradiation operation may be disposed at an upper end of the first handle part 212. The first connecting cable 220 may be for electrically and physically connecting the first operation handpiece 210 to the equipment main body 100. One end of the first connecting cable 220 may be connected to the first operation handpiece 210, and the other end may be attachably and detachably connected to the equipment main body 100 by connecting type.

The first cartridge set 300 may be a set consisting of a plurality of cartridges. For example, the first cartridge set 300 may include a first cartridge 310 and a second cartridge 320 which have operation conditions different from each other. The first cartridge 310 and the second cartridge 320 are cartridges with operation objectives different from each other. Specifically, the first cartridge 310 may be for non-invasive operation for reducing or removing subcutaneous fat, and the second cartridge 320 may be for non-invasive face lifting or skin tightening operation. An operation process, operation conditions, and the like of each of the first cartridge 310 and the second cartridge 320 will be described in detail below.

Each of the first cartridge 310 and the second cartridge 320 may be configured to be attachable to and detachable from the first operation handle 210. For example, a first guide part 214 for engaging with a cartridge (310 and the like in FIG. 2) of the first cartridge set 300 may be disposed at a front end of the first handle part 212. In one embodiment, the first guide part 214 may be provided in the shape of a bar protruding toward the front end of the first handle part 212. Also, a through-hole 312a in the form corresponding to that of a cross-section of the first guide part 214 may be provided in a central area of a first cartridge body 312. Consequently, as illustrated in FIG. 2(a), by the first guide part 214 being inserted into the through-hole 312a, the first cartridge 310 may be installed in the first operation handpiece 210. Here, to prevent the installed state of the first cartridge 310 from being released, a locking device 214a may be disposed at a front end of the first guide part 214, and the operator may lock or unlock the first cartridge 310 by rotating the locking device 214a.

A first imaging probe 216 for imaging operation target tissue may be provided inside the first guide part 214. The first imaging probe 216 may be provided mostly in the shape of a bar along the first guide part 214. The first imaging probe 216 may generate imaging ultrasound so that skin tissue to be treated, i.e., subcutaneous fat layer, can be imaged. The first guide part 214 may be provided to be placed on an upper portion of a treatment transducer 314 disposed in each of the first cartridge 310 and the second cartridge 320 when the first cartridge 310 and the second cartridge 320 are engaged with the first operation handle 210. Accordingly, the treatment transducer 314 may perform a function of irradiating focused ultrasound while moving back and forth at a lower portion of the first guide part 214, and accordingly, the treatment transducer 314 may also be referred to as an ultrasound treatment part. Also, the first imaging probe 216 may generate separate imaging ultrasound to image subcutaneous fat and display subcutaneous fat on the display 110.

Here, for back and forth movement of the treatment transducer 314, a first driving device 218 may be disposed in the first operation handpiece 210. In one embodiment, a stepping motor or the like may be used as the first driving device 218, and the first driving device 218 and the treatment transducer 314 may be connected to each other by a support 316. Accordingly, by the first driving device 218 moving the support 316 back and forth, the treatment transducer 314 may be moved back and forth.

The first driving device 218 may move the treatment transducer 314 back and forth so that the treatment transducer 314 has an operation section of about 40.0 mm to 100.0 mm. More specifically, the first driving device 218 may be provided as a stepping motor, and allow the treatment transducer 314 to be moved back and forth by a selected length within the range of about 40.0 mm to 100.0 mm. Here, the first driving device 218 illustrated in FIG. 3 may be a coaxial cross-section of the stepping motor. Here, the treatment transducer 314 may irradiate focused ultrasound while moving within the range. The treatment transducer 314 may be set to irradiate focused ultrasound at predetermined intervals so that thermal focal points 12 form a plurality of dots along the same line, or may be set to irradiate focused ultrasound so that the thermal focal points 12 form a straight line without intervals.

When a back-and-forth movement length of the treatment transducer 314 is less than 40.0 mm, because an operation area for skin lifting, skin tightening, or subcutaneous fat is small, an operation time may be extremely increased. Also, because subcutaneous fat is spread to be curved in both directions from a person's navel, when the back-and-forth movement range of the treatment transducer 314 exceeds 100.0 mm, the treatment transducer 314 is set to irradiate focused ultrasound to a predetermined depth. Thus, because an initial depth of irradiating subcutaneous fat with focused ultrasound and a final depth of irradiating subcutaneous fat with focused ultrasound become different, danger in that an area deviated from subcutaneous fat is irradiated with focused ultrasound may be increased. Such danger may occur similarly in the viewpoint of skin lifting or skin tightening. Consequently, the treatment transducer 314 being set to be movable back and forth within the range of about 40.0 mm to 100.0 mm, more preferably, within the range of 60.0 mm to 80.0 mm, may be more suitable for the first driving device 218 to secure operation safety and shorten operation time.

A cooling fluid for cooling heat generated due to operation of the treatment transducer 314 may be provided in each of the first cartridge 310 and the second cartridge 320. In one embodiment, each of the first cartridge 310 and the second cartridge 320 may be provided to have coolant filled therein, and the coolant may circulate by a separate coolant circulation line (not illustrated) to prevent overheating of the treatment transducer 314. For this, when the first cartridge 310 and the second cartridge 320 are installed in the first operation handpiece 210, the coolant in the first cartridge 310 and the second cartridge 320 may be connected to the coolant circulation line, and the coolant circulation line may be connected to a coolant storage container (not illustrated) inside the equipment main body 100 and circulate the coolant inside the coolant storage container. Although not illustrated, a circulator such as a pump may be installed on the coolant circulation line.

In the focused ultrasound operation apparatus 10 having the above structure, because the first cartridge 310 and the second cartridge 320 having conditions suitable for different types of operations can be selectively installed in the first operation handpiece 210, the operator may select a cartridge capable of performing desired operation from the first cartridge 310 and the second cartridge 320 and install the selected cartridge in the first operation handpiece 210 to perform operation. In this case, compared to a focused ultrasound medical device capable of performing only one type of operation, because the focused ultrasound operation apparatus 10 can perform various types of operations just by replacing a cartridge within a single piece of equipment, a structure of a multi-purpose ultrasound medical device can be realized.

Particularly, in cases of non-invasive ultrasound operation for face lifting and non-invasive ultrasound operation for reducing subcutaneous fat, because depth and intensity conditions of focused ultrasound and skin tissue to be imaged, etc. are completely different, it has been extremely difficult to perform such two types of operations by a single piece of equipment. However, by having the first imaging probe 216 which is shared by the first cartridge 310 and the second cartridge 320 which are of different types in the first operation handpiece 210 and then allowing different types of operations to be performed by replacing the first cartridge 310 and the second cartridge 320, the focused ultrasound operation apparatus 10 eliminates the above technical barrier.

As described above, by the focused ultrasound operation apparatus 10 according to an embodiment of the present invention having the first cartridge set 300 consisting of the first cartridge 310 and the second cartridge 320 which have different operation objectives and then a cartridge capable of performing desired operation being selected from the first cartridge 310 and the second cartridge 320 and installed in the first operation handpiece 210, desired operation can be performed for each operation objective. Accordingly, by having operation handpieces which have various operation objectives and then performing operation using an operation handpiece for desired operation of face lifting or skin tightening operation and operation for reducing or removing subcutaneous fat, the focused ultrasound operation apparatus according to the present invention may perform two or more types of focused ultrasound operation by single piece of equipment. Also, by having cartridges which have operation conditions suitable for an operation target's state and are compatible to an operation handpiece and then being able to perform operation by installing a selected cartridge in the operation handpiece, the focused ultrasound operation apparatus according to an embodiment of the present invention can perform patient-tailored operation using single piece of equipment by replacing a cartridge.

Next, the first cartridge set 300 according to an embodiment of the present invention will be described in detail. Here, description overlapping with the above description of the focused ultrasound operation apparatus 10 may be omitted or simplified.

Figure 4:
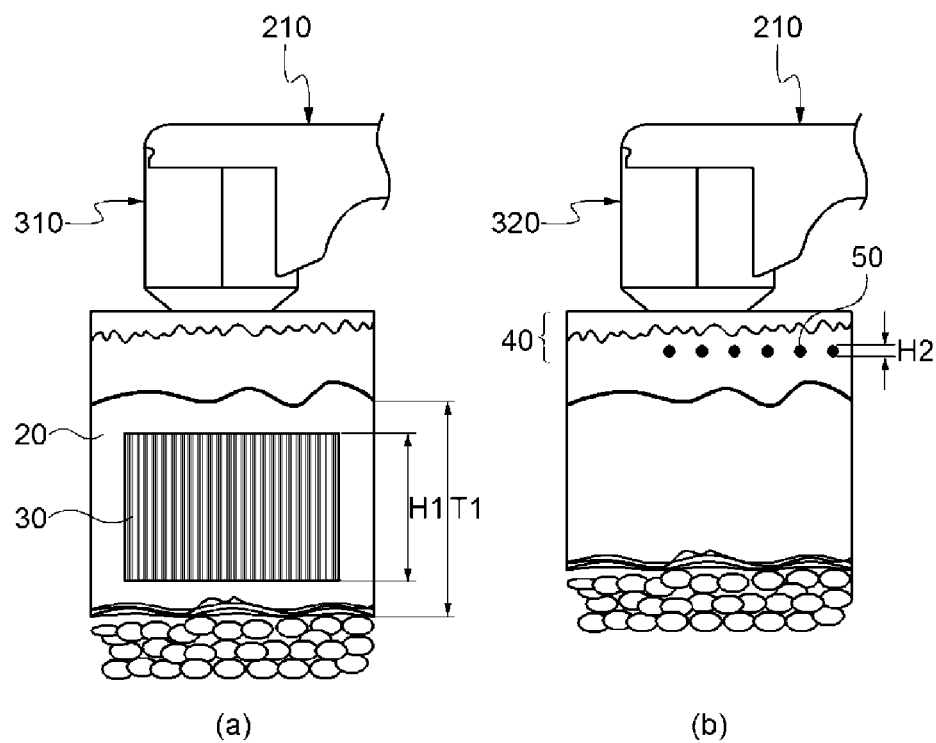
FIG. 4 illustrates views for describing first and second cartridges according to an embodiment of the present invention.

FIG. 4 is a view for describing the first cartridge 310 and the second cartridge 320 according to an embodiment of the present invention. More specifically, FIG. 4(a) is a view for describing operation conditions of the first cartridge 310 according to an embodiment of the present invention, and FIG. 4(b) is a view for describing operation conditions of the second cartridge 320 according to an embodiment of the present invention.

Referring to FIG. 4(a), the first cartridge 310 according to an embodiment of the present invention may be for operation of reducing or removing subcutaneous fat. In one embodiment, the first cartridge 310 may be used when a thickness T1 of subcutaneous fat 20 to be treated is 25.0 mm or larger. That is, the first cartridge 310 may have been set to have a condition in which operation can be performed when the thickness T1 of the subcutaneous fat 20 is at least 25.0 mm. In this case, it is highly likely that a patient receiving operation is an extremely obese patient. The first cartridge 310 may be controlled so that a vertical length H1 of a thermal focal point 30 of focused ultrasound is about 8.0 mm to 12.0 mm and an irradiation depth of focused ultrasound from skin surface is about 11.0 mm to 15.0 mm. When the vertical length H1 of the thermal focal point 30 is less than about 8.0 mm, efficiency of reducing the subcutaneous fat 20 may be decreased. Conversely, when the vertical length H1 of the thermal focal point 30 exceeds about 12.0 mm, the thermal focal point may be formed in an area deviated from the subcutaneous fat 20. Also, when the irradiation depth is less than about 11.0 mm or exceeds about 15.0 mm, the thermal focal point 30 may deviate from the subcutaneous fat 20 during operation. Consequently, when the vertical length H1 of the thermal focal point 30 is controlled to be about 8.0 mm to 12.0 mm, and the irradiation depth of focused ultrasound is controlled to be 11.0 mm to 15.0 mm, the treatment transducer 314 of the first cartridge 310 may decrease danger in that operation is performed on skin tissue other than the subcutaneous fat 20 even when operation is performed in the case in which the thickness T1 of the subcutaneous fat 20 is 25.0 mm or larger.

In another embodiment, the first cartridge 310 may be used when the thickness T1 of the subcutaneous fat 20 to be treated is 7.0 mm or larger and less than 25.0 mm. That is, the first cartridge 310 may have been set to have a condition in which operation can be performed when the thickness T1 of the subcutaneous fat 20 is at least 7.0 mm but smaller than 25.0 mm. In this case, it is highly likely that a patient receiving operation is a mildly obese patient. In this case, the first cartridge 310 may be controlled so that the vertical length H1 of the thermal focal point 30 is about 5.0 mm to 9.0 mm and the irradiation depth of focused ultrasound from skin surface is about 6.0 mm to 10.0 mm. When the vertical length H1 of the thermal focal point 30 is less than about 5.0 mm, efficiency of reducing the subcutaneous fat 20 may be decreased. Conversely, when the vertical length H1 of each of the thermal focal points 30 exceeds about 9.0 mm, the thermal focal point 30 may be formed in an area deviated from the subcutaneous fat 20. Also, when the irradiation depth is less than about 6.0 mm or exceeds about 10.0 mm, the thermal focal point 30 may deviate from the subcutaneous fat 20 during operation. Consequently, when the vertical length H1 of the thermal focal point 30 is controlled to be about 5.0 mm to 9.0 mm, and the irradiation depth of focused ultrasound is controlled to be 6.0 mm to 10.0 mm, the treatment transducer 314 of the first cartridge 310 may decrease danger in that operation is performed on skin tissue other than the subcutaneous fat 20 even when operation is performed in the case in which the thickness T1 of the subcutaneous fat 20 is 7.0 mm or larger and less than 25.0 mm.

Here, the treatment transducer 314 of the first cartridge 310 may move back or forth, i.e., linearly reciprocate, and allow a plurality of thermal focal points 30 to be generated. Here, intervals between the thermal focal points 30 may be none or less than 1.0 mm so that the thermal focal points 30 form a linear or column-like shape that is not broken throughout and thermally break down the subcutaneous fat 20. However, when the thermal focal points 30 overlap each other, because a person on which operation is performed may feel great pain, it may be ideal for focused ultrasound to be irradiated while the thermal focal points 30 are maximally adjacent to each other under a condition of not overlapping each other.

Referring to FIG. 4(b), unlike the first cartridge 310 described above, the second cartridge 320 according to an embodiment of the present invention may be for face lifting or skin tightening operation. In one embodiment, skin tissue 40 to be treated of the second cartridge 320 may include dermis, fascia, and SMAS layer at a depth of about 1.5 mm to 4.5 mm from skin surface. Here, the second cartridge 320 may be controlled so that thermal focal points 50 are generated mostly in a spherical shape, an elliptical shape, or a drop shape having a diameter of about 0.5 mm to 1.5 mm. When the diameter of the thermal focal point 50 is less than about 0.5 mm, because damage to focused ultrasound target tissue is very small, it may be difficult to obtain a face lifting or skin tightening effect through regeneration after intentional damage to skin. Conversely, when the diameter of the thermal focal point 50 exceeds 1.5 mm, the thermal focal point 50 may be formed in an area deviated from the skin tissue 40 to be treated. Also, when the irradiation depth is less than about 1.5 mm or exceeds about 4.5 mm, the thermal focal point 50 may deviate from the skin tissue 40 to be treated during operation. Consequently, the treatment transducer 314 of the second cartridge 320 is preferably controlled so that the diameter of the thermal focal point 50 is about 0.5 mm to 1.5 mm, and the irradiation depth of focused ultrasound is about 1.5 mm to 4.5 mm. Most preferably, the irradiation depth of the thermal focal point 50 is any one selected from 1.5 mm, 3.0 mm, and 4.5 mm, and the diameter of the thermal focal point 50 is set to be about 1.0 mm.

Here, the treatment transducer of the second cartridge 320 may allow a plurality of thermal focal points 50 to be generated while moving back or forth, i.e. linearly reciprocating. Here, the interval between the thermal focal points 50 may be about 0.5 mm to less than 2.0 mm so that the thermal focal points 50 are spaced apart at equal intervals and are controlled to form a plurality of dots spaced apart from each other along the same line. When the interval between the thermal focal points 50 is less than 0.5 mm, the thermal focal points 50 are connected to each other as a result, and a problem such as dermal necrosis may occur due to excessive thermal damage to skin tissue. Conversely, when the interval between the thermal focal points 50 exceeds 2.0 mm, because the interval between the thermal focal points 50 is too large, a face lifting or skin tightening effect may be considerably decreased as a result.

Next, an operation method using the above-described first operation handpiece of the focused ultrasound according to an embodiment of the present invention will be described in detail. Here, description overlapping with the above description of the focused ultrasound operation apparatus 10 according to an embodiment of the present invention may be omitted or simplified.

Figure 5:
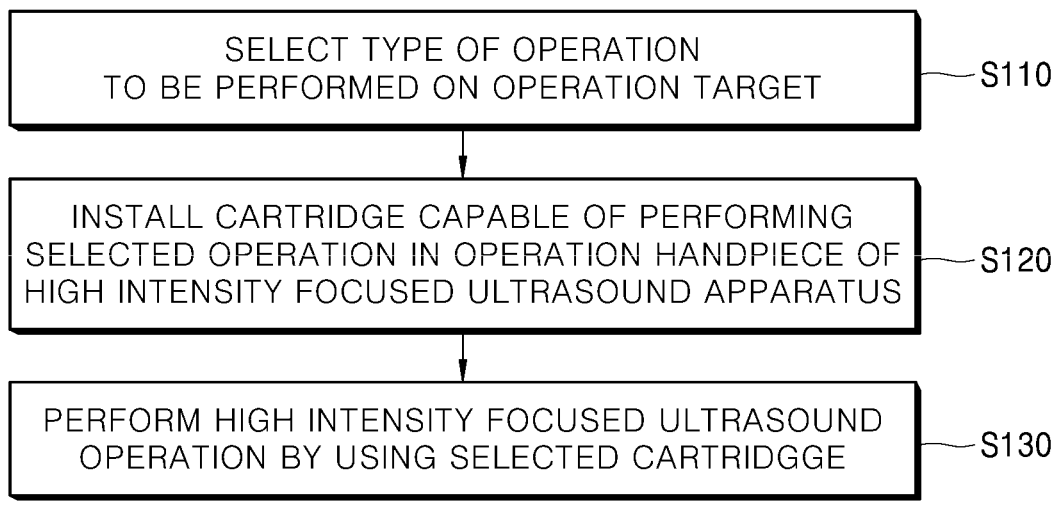
FIG. 5 is a view for describing a process of performing operation using the first operation handle illustrated in FIG. 1.

FIG. 5 is a view for describing a process of performing operation using the first operation handle illustrated in FIG. 1. Referring to FIGS. 1 to 5, first, a type of operation to be performed on an operation target may be selected (S110). For example, an operator (not illustrated) may select a type of operation to be performed on an operation target (not illustrated). Here, a type of operation that may be selected may include at least one of face lifting or skin tightening operation and operation for reducing or removing subcutaneous fat. When the operator wants to perform operation for reducing or removing subcutaneous fat, the operator may select the first cartridge 310 according to the above-described embodiment or another embodiment in consideration of thickness of subcutaneous fat, depth of subcutaneous fat, and other conditions of the operation target. Here, to check the thickness of subcutaneous fat, the operator may directly perceive the thickness of subcutaneous fat by hand or check subcutaneous fat imaged by the imaging probe 216 disposed in the first operation handpiece 210 and calculate precise thickness of subcutaneous fat.

Then, the operator may select a cartridge capable of performing the selected operation and install the selected cartridge in the first operation handpiece 210 of the focused ultrasound operation apparatus 10 (S120). For example, when the operator wants to perform operation of reducing or removing subcutaneous fat, the operator may select the first cartridge 310 from the first cartridge set 300 and install the first cartridge 310 in the first operation handpiece 210. Alternatively, when the operator wants to perform face lifting or skin tightening operation, the operator may select the second cartridge 320 from the first cartridge set 300 and install the second cartridge 320 in the first operation handpiece 210.

Then, the operator may perform focused ultrasound operation using the selected cartridge (S130). For example, the operator may use the first operation handpiece 210 in which any one of the first cartridge 310 and the second cartridge 320 is installed and perform face lifting or skin tightening operation and operation for reducing or removing subcutaneous fat on the operation target.

As described above, in the operation method using the focused ultrasound according to an embodiment of the present invention, a type of operation to be performed on an operation target may be selected, the first cartridge 310 or the second cartridge 320 capable of performing the desired operation may be selected from the first cartridge set 300, and then operation may be performed by installing the selected cartridge in the first operation handpiece 210. Accordingly, in the operation method using the focused ultrasound according to the present invention, by preparing cartridges having various operation objectives to be compatible with an operation handpiece, and then performing operation by installing a cartridge for desired operation of face lifting or skin tightening operation and operation for reducing or removing subcutaneous fat in the operation handpiece, two or more types of focused ultrasound operation can be performed using a single piece of equipment. Further, operation may also be performed by installing a cartridge for desired operation of gynecological disease treatment and vaginal tightening operation in the operation handpiece. Also, by preparing skin care treatment cartridges having various operation conditions to be compatible with an operation handpiece, and then performing operation for reducing subcutaneous fat by installing a cartridge having a condition that fits an operation target's state of obesity or treatment site in the operation handpiece, the operation method using the focused ultrasound according to the present invention may perform customized operation for each patient or each site.

Hereinafter, the second operation handpiece of the focused ultrasound operation apparatus according to an embodiment of the present invention and a process of gynecological disease treatment and/or vaginal tightening operation using the same will be described in detail. Here, description overlapping with the above description of the focused ultrasound operation apparatus 10 may be omitted or simplified.

Figure 6:
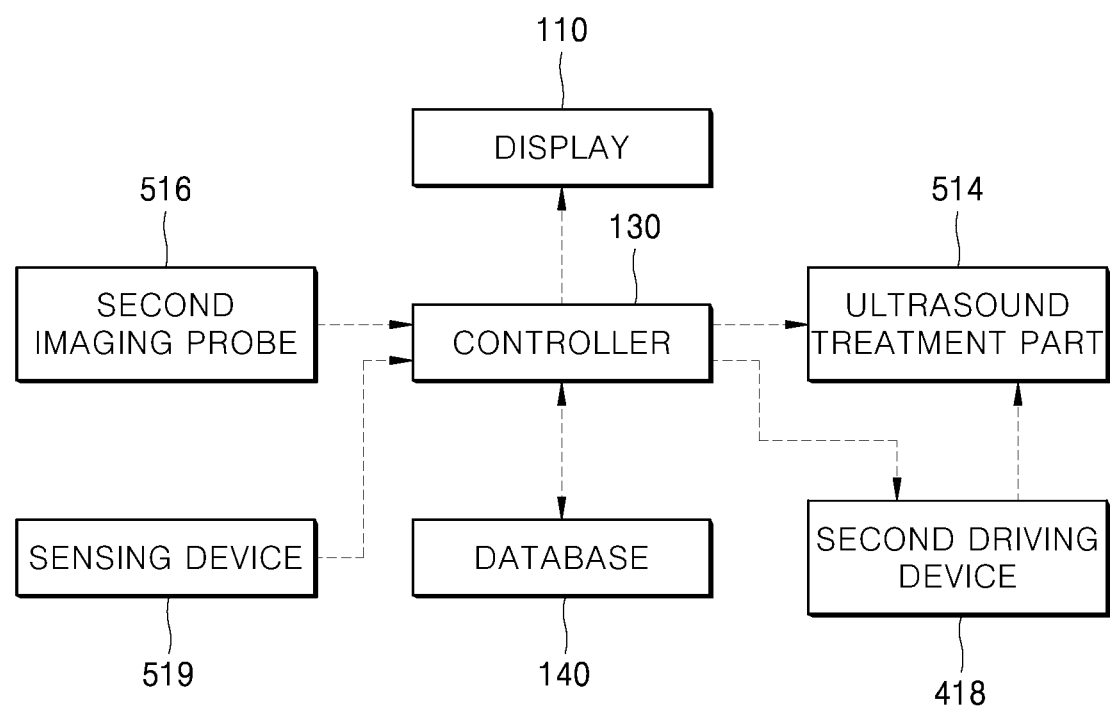
FIG. 6 is a view for describing an operating principle of the focused ultrasound operation apparatus according to an embodiment of the present invention that uses a second operation handpiece and a third cartridge.
Figure 7:
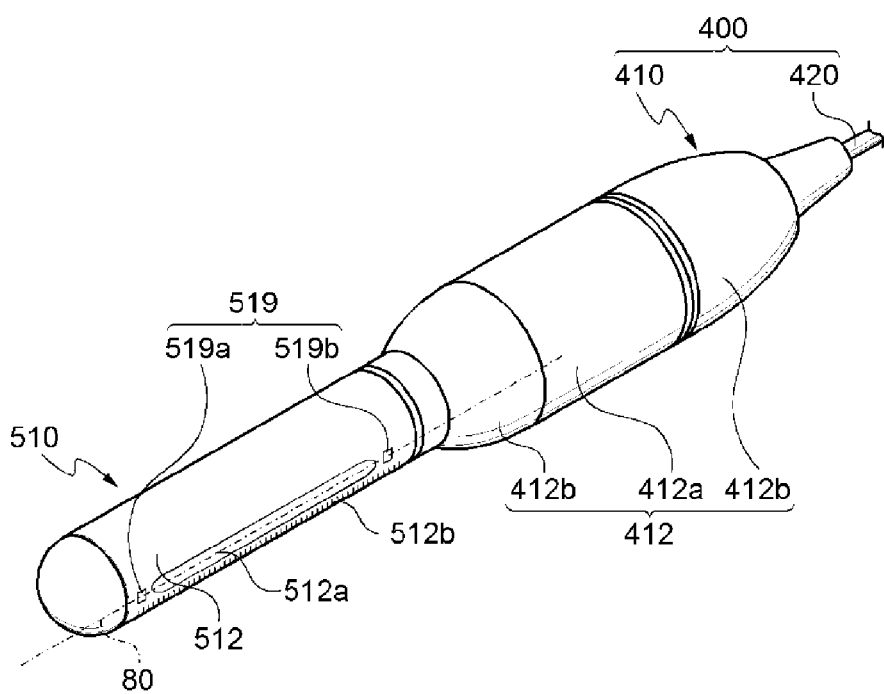
FIG. 7 is a perspective view illustrating the second operation handpiece and the third cartridge illustrated in FIG. 1.
Figure 8:
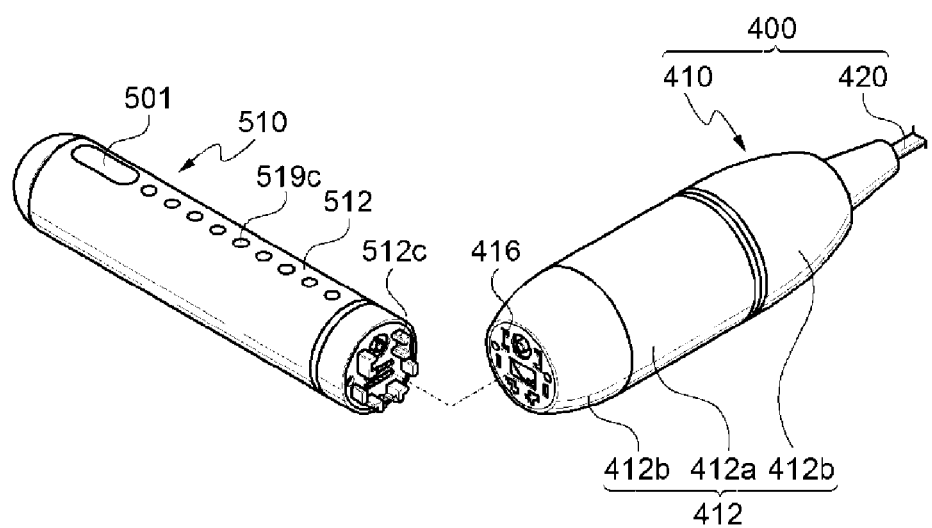
FIG. 8 is a view for describing a coupling process between the second operation handpiece and the third cartridge illustrated in FIG. 7.
Figure 9:
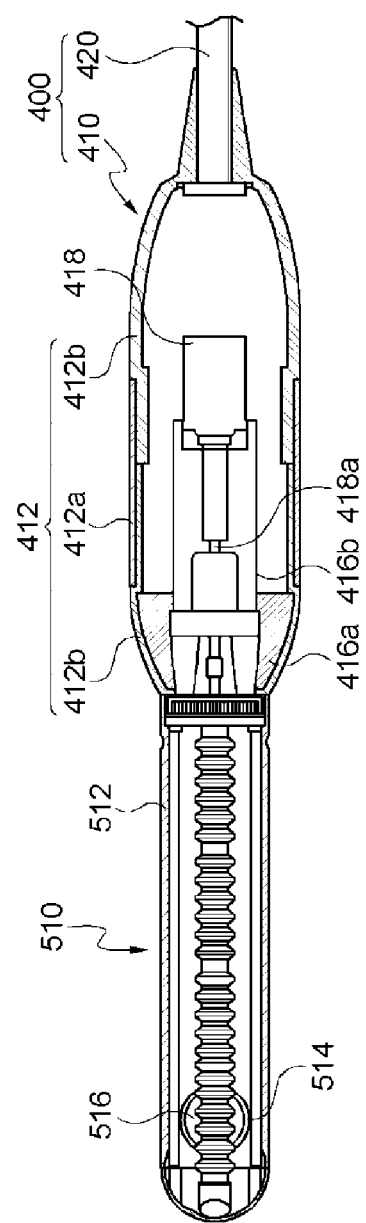
FIG. 9 is a first cross-sectional view illustrating a coupling structure between the second operation handpiece and the third cartridge illustrated in FIG. 7.
Figure 10:
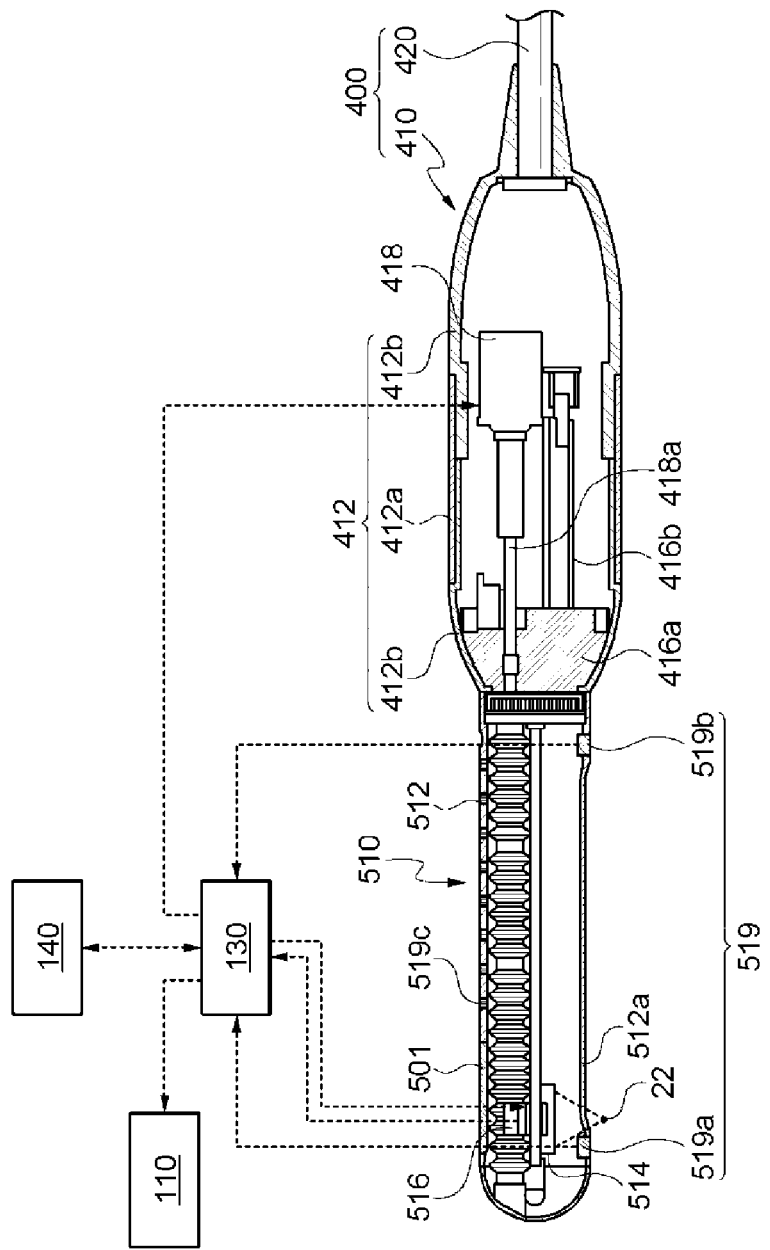
FIG. 10 is a second cross-sectional view illustrating the coupling structure between the second operation handpiece and the third cartridge illustrated in FIG. 7.
Figure 11:
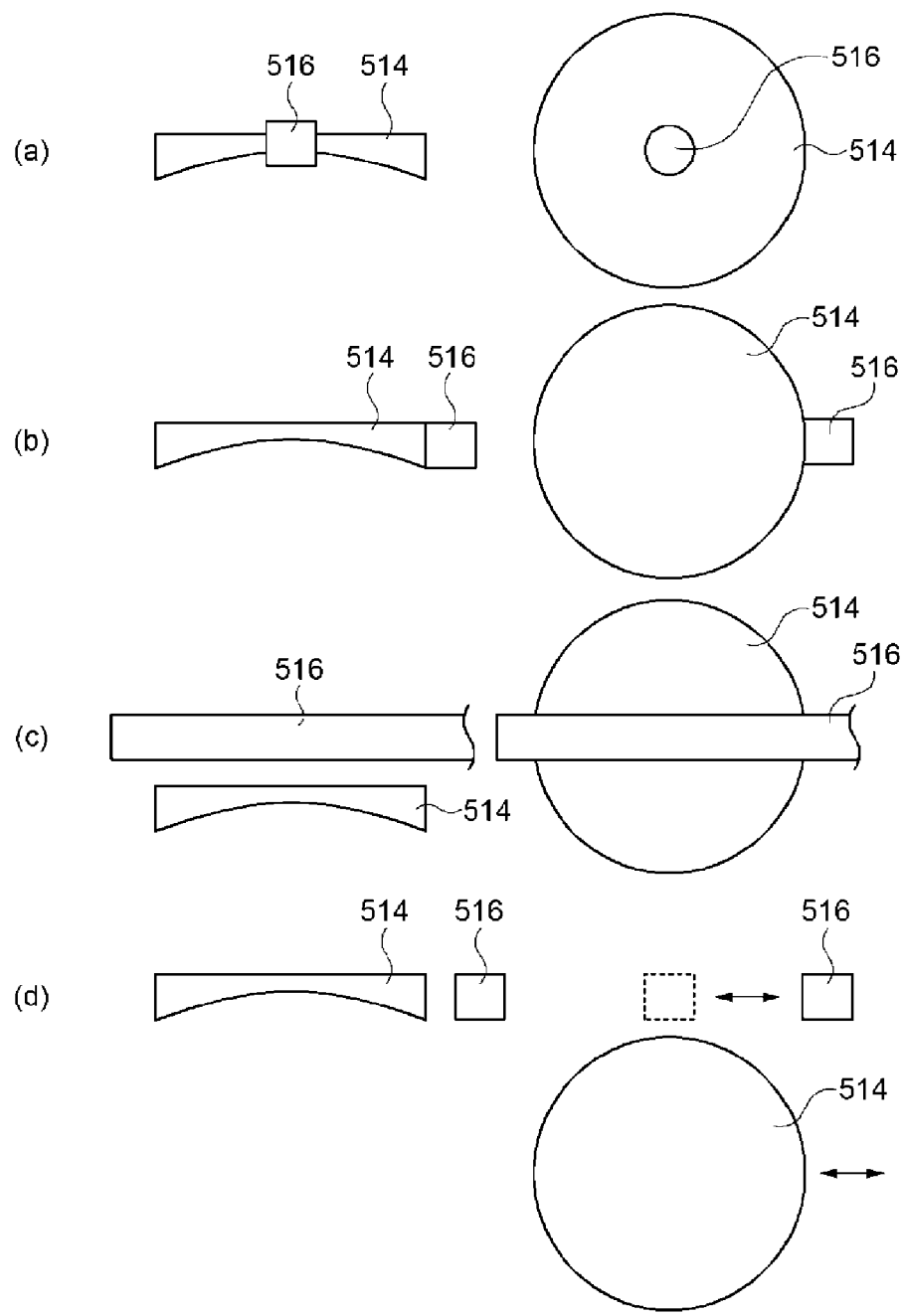
FIG. 11 illustrates views for describing various examples of an arrangement structure of an ultrasound treatment part and an imaging probe illustrated in FIG. 7.

FIG. 6 is a view for describing an operating principle of the focused ultrasound operation apparatus according to an embodiment of the present invention that uses a second operation handpiece and a third cartridge, FIG. 7 is a perspective view illustrating the second operation handpiece and the third cartridge illustrated in FIG. 1, and FIG. 8 is a view for describing a coupling process between the second operation handpiece and the third cartridge illustrated in FIG. 7. FIG. 9 is a first cross-sectional view illustrating a coupling structure between the second operation handpiece and the third cartridge illustrated in FIG. 7, and FIG. 10 is a second cross-sectional view illustrating the coupling structure between the second operation handpiece and the third cartridge illustrated in FIG. 7. FIG. 11 illustrates views for describing various examples of an arrangement structure of an ultrasound treatment part and an imaging probe illustrated in FIG. 7.

Referring to the drawings, the second handpiece assembly 400 and the second cartridge set 500 of the focused ultrasound operation apparatus 10 according to an embodiment of the present invention may perform gynecological disease and/or vaginal tightening operation by using focused ultrasound.

The gynecological disease and vaginal tightening operation may include operation for treating tumors, neoplastic disease, inflammatory disease, menstrual disorder, venereal disease, and sexual dysfunction. For example, to treat sexual decline or dysfunction due to parturition or aging, the focused ultrasound operation apparatus 10 for the gynecological disease treatment and vaginal tightening operation may perform operation in which skin tissue at a depth of about 0.5 mm to 3.0 mm from skin surface of vagina 60 (see FIG. 18) is intentionally damaged or stimulated and then restored to normal tissue by densification or regeneration of the skin tissue. In another example, to treat sexual decline or dysfunction due to parturition or aging, the focused ultrasound operation apparatus 10 for the gynecological disease treatment and vaginal tightening operation may perform operation in which the EPF 70 (see FIG. 18) responsible for contraction motion of the vagina 60 (see FIG. 18) is densified or regenerated.

Here, the focused ultrasound may be for focusing ultrasound waves to be gathered at one focal point to form a thermal focal point 22. The thermal focal point 22 may be a thermal focal point in a high-temperature state of about 60° C. or higher. Consequently, the focused ultrasound operation apparatus 10 may perform operation in which the thermal focal point 22 is formed on tissue adjacent to skin surface of the vagina 60, e.g., skin tissue within the range of about 0.5 mm to 3.0 mm from the skin surface of the vagina, to intentionally damage or stimulate the skin tissue, and then the skin tissue is restored to normal tissue by densification or regeneration of the skin tissue. Alternatively, the focused ultrasound operation apparatus 10 may improve contraction force of the vagina 60 by forming the thermal focal point 22 on the EPF 70 placed at a depth of about 1.0 to 30.0 mm from an inner surface 62 (see FIG. 18) of the vagina 60, intentionally damaging or stimulating the EPF 70, and then promoting restoration or regeneration of the EPF 70.

The above-described focused ultrasound operation apparatus 10 for gynecological disease treatment and/or vaginal tightening operation may include the display 110, a controller 130, a database 140, an ultrasound treatment part 514, a second imaging probe 516, and a sensing device 519.

The display 110 may include an imaging device configured to display information on the gynecological disease treatment and/or vaginal tightening operation to the operator. The controller 130 may compare imaged data captured by the second imaging probe 516 with reference data stored in the database 140 and provide the operator with information required for operation. For example, pieces of reference data related to average thickness of muscle of women vagina, position or depth of vaginal muscle, and skin tissue at a predetermined depth for forming the thermal focal point 22 from skin surface of vagina may be stored in the database 140. Also, the second imaging probe 516 may measure thickness, position, or depth of vagina of an operation target and send the measured thickness, position, or depth to the controller 130, and the controller 130 may compare the transmitted imaged data with the reference data and display information required for operation on the display 110.

Also, the focused ultrasound operation apparatus 10 may further include the sensing device 519 configured to sense whether a cartridge (e.g., a third cartridge 510) having the ultrasound treatment part 514 embedded therein is normally placed at a preset position on an inner wall of the vagina 60 during operation. The sensing device 519 is for using various sensing technologies to sense whether the cartridge is normally placed so that the ultrasound treatment part 514 precisely forms the thermal focal point 22 on skin tissue on which operation is desired to be performed, and the controller 130 may determine sensed data of the sensing device 519 and control the ultrasound treatment part 514. Reference data for determining the sensed data of the sensing device 519 may be further stored in the database 140.

Next, a detailed embodiment of the above-described focused ultrasound operation apparatus 10 will be described. Here, detailed description of the equipment main body 100 or the like which is commonly applied to other operation will be omitted or simplified.

Referring to FIGS. 1 and 6 to 11, the focused ultrasound operation apparatus 10 according to an embodiment of the present invention may include the second handpiece assembly 400 and the second cartridge set 500.

The second handpiece assembly 400 may include a second operation handpiece 410 and a second connecting cable 420. The second operation handpiece 410 may be manipulated by the operator to irradiate an operation target with focused ultrasound and may be provided in a hand-held form to improve convenience of user manipulation. For example, the second operation handpiece 410 may include a second handle part 412 so that the operator can hold the second operation handpiece 410. A second operation switch (not illustrated) configured to allow the operator to control ultrasound irradiation operation may be disposed in the second handle part 412. The second connecting cable 420 may be for electrically and physically connecting the second operation handpiece 410 to the equipment main body 100. One end of the second connecting cable 420 may be connected to the second operation handpiece 410, and the other end may be attachably and detachably connected to the equipment main body 100 by connecting type.

The second cartridge set 500 may be a set consisting of a plurality of cartridges. For example, the second cartridge set 500 may include the third cartridge 510, a fourth cartridge 520, and a fifth cartridge 530 having structures which are the same as or similar with each other. Each of the third cartridge 510, the fourth cartridge 520, and the fifth cartridge 530 may be provided as an insertion part that is inserted into the vagina 60 during operation and may also be provided as a focused ultrasound irradiation part configured to irradiate skin tissue at a predetermined depth from an inner wall surface of the vagina 60 with focused ultrasound.

For example, the third cartridge 510, the fourth cartridge 520, and the fifth cartridge 530 may have the same operation objective and conditions. That is, the third cartridge 510, the fourth cartridge 520, and the fifth cartridge 530 may be set to have the same specific irradiation intensity, depth, and angle of focused ultrasound and the same conditions for size and formation position of the thermal focal point 22 formed by the focused ultrasound. Accordingly, each of the third cartridge 510, the fourth cartridge 520, and the fifth cartridge 530 may irradiate an inner wall of a woman's vagina with focused ultrasound under the same or similar conditions during operation and form the thermal focal point 22. The operator may continuously perform the gynecological disease treatment by installing the third cartridge among the third cartridge 510, the fourth cartridge 520, and the fifth cartridge 530 in the second operation handpiece 410 to use the third cartridge 510 and, when a use period of the third cartridge 510 is expired, using the fourth cartridge 520 or the fifth cartridge 530 instead of the third cartridge 510.

In another example, the third cartridge 510, the fourth cartridge 520, and the fifth cartridge 530 may have different operation objectives or conditions. For example, the third cartridge 510 may be set to form a relatively large thermal focal point of focused ultrasound, and the fourth cartridge 520 may be set to form a relatively small thermal focal point of focused ultrasound compared to the third cartridge 510. Further, the fifth cartridge 530 may be set to form a relatively small thermal focal point of focused ultrasound compared to the fourth cartridge 520. Alternatively, the third cartridge 510 may be set to form the thermal focal point 22 on skin tissue at a small depth from the inner surface 62 of the vagina, and the fourth cartridge 520 may be set to form the thermal focal point 22 on skin tissue at a relatively large depth from the inner surface 62 of the vagina compared to the third cartridge 510. Further, the fifth cartridge 530 may be set to form the thermal focal point 22 on skin tissue at a relatively larger depth from the inner surface 62 of the vagina compared to the fourth cartridge 520.

As described above, because the third cartridge 510, the fourth cartridge 520, and the fifth cartridge 530 have similar structures, for describing detailed configurations thereof, the third cartridge 510 will be described in detail as an example to substitute for description of the remaining cartridges 520 and 530.

The third cartridge 510 may have a mostly cylindrical or bar-shaped second cartridge body 512. The second cartridge body 512 is preferably provided to have a form and material that may easily be inserted into the vagina 60 of a woman. Accordingly, a front end of the second cartridge body 512 may protrude in a convex shape, and a circumference thereof may be rounded in an oblique curve. Also, the second cartridge body 512 may be formed of a material that is harmless to the human body and has high durability and wear resistance.

A window 512a provided along a longitudinal direction of the second cartridge body 512 may be disposed at the circumference of the second cartridge body 512. The window 512a may be formed of a material having high ultrasound transmittance so that focused ultrasound generated from the ultrasound treatment part 514 disposed in the third cartridge 510 can be efficiently transmitted. Also, scales 512b provided along the longitudinal direction of the second cartridge body 512 may be provided at the circumference of the second cartridge body 512. The scales 512b may be provided to allow the operator to figure out an extent to which the second cartridge body 512 is inserted into the vagina. Further, additional scales (not illustrated) provided along the circumferential direction of the second cartridge body 512 may be provided at the circumference of the second cartridge body 512. The additional scales may be provided to allow the operator to figure out a degree of rotation or the like of the second cartridge body 512. Although the scales 512b are described as an example of a means for allowing the operator to estimate the extent to which the second cartridge body 512 is inserted in this embodiment, the means for estimating the extent to which the second cartridge body 512 is inserted may be changed or modified in various ways.

The third cartridge 510 may be configured to be attachable to and detachable from the second operation handpiece 410. For example, a second guide part 416 for engaging with the third cartridge 510 may be disposed at a front end of the second handle part 412. In one example, the second guide part 416 may be provided as a hole or groove recessed toward a rear end of the second handle part 412. Also, an engaging part 512c having the shape corresponding to that of the second guide part 416 may be provided at a part of the second cartridge body 512 coupled to the second guide part 416. The engaging part 512c may be provided as a bar-shaped structure protruding to be inserted into the second guide part 416. In this case, the second guide part 416 and the engaging part 512c may be coupled, detached, or rotated by a forcibly fitting method, a screw bolt method, or simple coupling method in which rotation is possible. Accordingly, by inserting the engaging part 512c into the second guide part 416, the third cartridge 510 may be installed in the second operation handpiece 410. In one embodiment, the engaging part 512c may be coupled to be rotatable by 360° in the state of being inserted into the second guide part 416. Here, to prevent the installed state of the third cartridge 510 from being released, a separate locking device (not illustrated) may be disposed in the second operation handpiece 410 or in each of the third cartridge 510, the fourth cartridge 520, and the fifth cartridge 530.

The ultrasound treatment part 514 may be disposed in the third cartridge 510. The ultrasound treatment part 514 may include at least one ultrasound transducer configured to generate the focused ultrasound. For example, as illustrated in FIGS. 9 and 10, the ultrasound treatment part 514 may include at least one independent transducer configured to form a single thermal focal point of focused ultrasound. In this case, the independent transducer may be configured to irradiate the focused ultrasound while moving along the window 512a. In another example, the ultrasound treatment part 514 may include at least one transducer array configured to form multiple thermal focal points of focused ultrasound at a predetermined depth from the inner wall of the vagina 60. That is, the transducer array may be designed so that a plurality of thermal focal points 22 are formed from a single transducer body. In this case, the transducer array may be installed to not move and be fixed to an inside of the second cartridge body 512 or designed to move a small distance compared to the independent transducer.

The second imaging probe 516 configured to image skin tissue which is operation target may be provided in each of the third cartridge 510, the fourth cartridge 520, and the fifth cartridge 530. The second imaging probe 516 is for imaging skin tissue on which the thermal focal point 22 is formed, and configuration, arrangement, and the like thereof may be changed in various ways. For example, as illustrated in FIG. 11(a), the second imaging probe 516 may be coupled to the center of the ultrasound treatment part 514 and be integrally provided with the ultrasound treatment part 514. In this case, due to being disposed in a central area of the ultrasound treatment part 514, the imaging probe 516 may be disposed not to interfere with an irradiation path of focused ultrasound. In another example, as illustrated in FIG. 11(b), the second imaging probe 516 may be coupled to be adjacent to the circumference of the ultrasound treatment part 514. Here, the imaging probe 516 may be arranged on the same line as a movement direction of the ultrasound treatment part 514. In this case, the second imaging probe 516 may move in front of the ultrasound treatment part 514 or behind the ultrasound treatment part 514 and sequentially image skin tissue on which the thermal focal point 22 is formed. In still another example, as illustrated in FIG. 11(c), the second imaging probe 516 may be provided in the form of a long bar along the movement direction of the ultrasound treatment part 514. In this case, the second imaging probe 516 may image skin tissue on which the thermal focal point 22 I formed without interfering with back and forth movement of the ultrasound treatment part 514. Alternatively, as illustrated in FIG. 11(d), the second imaging probe 516 may be detached from the ultrasound treatment part 514 and separately provide. Here, the second imaging probe 516 may be disposed at a position at which the skin tissue to be treated can be imaged without interfering with the movement path of the ultrasound treatment part 514. For this, the second imaging probe 516 may be driven by a separate driving device (not illustrated) that is different from the driving device configured to drive the ultrasound treatment part 514.

The second operation handpiece 410 may further include a second driving device 418 for back and forth movement of the ultrasound treatment part 514. For example, a stepping motor or the like may be used as the second driving device 418, and driving thereof may be controlled by the above-described manipulation part 120. Also, the second driving device 418 and the ultrasound treatment part 514 may be connected to each other by a predetermined support. Accordingly, when the second driving device 418 is controlled by the manipulation part 120 and a driving axis 418a is moved back and forth, the support coupled to the driving shaft 418a may be moved, and the ultrasound treatment part 514 may move back and forth. In this way, the second driving device 418 may be provided to be shared by the third cartridge 510, the fourth cartridge 520, and the fifth cartridge 530 and move the ultrasound treatment part 514 of each of the third cartridge 510, the fourth cartridge 520, and the fifth cartridge 530 back and forth.

The second operation handpiece 410 may be configured so that the operator may rotate a cartridge coupled to the second operation handpiece 410 among the third cartridge 510, the fourth cartridge 520, and the fifth cartridge 530, i.e., the third cartridge 510 in the drawing, by a predetermined angle. For example, the third cartridge 510 may be rotated by 0° to 360° by manual manipulation of the operator on the second operation handpiece 410. More specifically, the second handle part 412 of the second operation handpiece 410 may include a fixing part 412a and a cartridge rotating part 412b. The fixing part 412a may be held by one hand (e.g., left hand) of the operator to fix a position of the second operation handpiece 410 during operation. The cartridge rotating part 412b may be rotatably disposed at the fixing part 412a and may be engaged with one end of the third cartridge 510 to rotate together with the third cartridge 510 coupled to the second operation handpiece 410. The cartridge rotating part 412b may be provided to be held by the other hand (e.g., right hand) of the operator to rotate the third cartridge 510 during operation. In the second operation handpiece 410 having the above-described structure, the operator holds the fixing part 412a with left hand and rotates the cartridge rotating part 412b by predetermined angle with right hand so that the third cartridge 510 rotates by 0° to 360° about an axis along the longitudinal direction of the third cartridge 510, and the thermal focal points 22 can be formed throughout inner wall of the vagina. In one embodiment, a frame fixing part 416a may be coupled to an inside of the cartridge rotating part 412b, the above-described second driving device 418 may be fixed to a frame 416b coupled to the frame fixing part 416a, and accordingly, the frame 416b and the second driving device 418 may rotate together when the cartridge rotating part 412b rotates.

In another example, the third cartridge 510 may be automatically rotated by 0° to 360° by a simple on/off operation of the operator on the second operation handpiece 410. More specifically, the second driving device 418 of the second operation handpiece 410 may rotate the third cartridge 510 by a predetermined angle about the longitudinal direction of the second cartridge body 512 as an axis of rotation. For this, the second driving device 418 may include a rotary motor configured to rotate the third cartridge 510. Accordingly, the second driving device 418 may rotate the third cartridge 510 inside the vagina 60 during operation so that the ultrasound treatment part 514 forms the thermal focal points 22 at predetermined intervals along the circumference of the inner wall of the vagina 60. The rotation of the cartridge may allow focused ultrasound operation to be performed throughout inner wall of the vagina 60 in short time. Here, for smooth rotation of the cartridge, the second guide part 416 and the engaging part 512*c* are preferably provided in forms not interfering with the rotation.

Also, the second driving device 418 may move the ultrasound treatment part 514 back and forth so that the ultrasound treatment part 514 has an operation section of about 10.0 mm to 120.0 mm. More specifically, the second driving device 418 may be provided as a stepping motor controlled by the manipulation part 120 and may allow the ultrasound treatment part 514 to be moved back and forth by a length selected within the range of about 10.0 mm to 120.0 mm. Here, the ultrasound treatment part 514 may irradiate focused ultrasound while moving within the range. The ultrasound treatment part 514 may be set to irradiate focused ultrasound at predetermined intervals so that the thermal focal points 22 form a plurality of dots along the same line or may be set to irradiate focused ultrasound so that the thermal focal points 22 form a straight line without an interval.

When a back-and-forth movement length of the ultrasound treatment part 514 is less than 10.0 mm, because an operation area is small in a single operation process, an operation time may be extremely increased. Conversely, in the case in which a length, form, etc. of the vagina 60 or the EPF 70 of a woman are taken into consideration, when the back-and-forth movement length of the ultrasound treatment part 514 exceeds 120.0 mm, danger in that skin tissue other than the EPF 70 may be irradiated with focused ultrasound. Consequently, the ultrasound treatment part 514 being set to be movable back and forth within the range of about 10.0 mm to 120.0 mm, more preferably, within the range of 20.0 mm to 100.0 mm, may be more suitable for the second driving device 418 to secure operation safety and shorten operation time.

Also, a cooling fluid for cooling heat generated due to operation of the ultrasound treatment part 514 may be provided in each of the third cartridge 510, the fourth cartridge 520, and the fifth cartridge 530. In one embodiment, each of the third cartridge 510, the fourth cartridge 520, and the fifth cartridge 530 may be provided to have coolant filled therein, and the coolant may circulate by a separate coolant circulation line (not illustrated) to prevent overheating of the ultrasound treatment part 514. For this, when the third cartridge 510, the fourth cartridge 520, and the fifth cartridge 530 are installed in the second operation handpiece 410, the coolant in the third cartridge 510, the fourth cartridge 520, and the fifth cartridge 530 may be connected to the coolant circulation line, and the coolant circulation line may be connected to a coolant storage container (not illustrated) inside the equipment main body 100 and circulate the coolant inside the coolant storage container. Although not illustrated, a circulator such as a pump may be installed on the coolant circulation line.

The third cartridge 510 may further include the sensing device 519 configured to sense whether the third cartridge 510 is normally placed at a preset position in the inner wall of the vagina 60 during operation and a determination part 130 (e.g., the controller 130) configured to receive sensed data from the sensing device 519 to determine whether the third cartridge 510 is normally placed and control operation conditions and the like. The determining of whether the third cartridge 510 is normally placed by the determination part 130 may be performed by determining whether the third cartridge 510 is in complete contact or is adhered to the inner wall of the vagina to be treated.

More specifically, the sensing device 519 may include a plurality of sensors arranged at different positions of the second cartridge body 512. For example, the sensing device 519 may include a first sensor 519*a* arranged at one side of the window 512*a* of the second cartridge body 512 and a second sensor 519*b* arranged at the other side of the window 512*a*. The first sensor 519*a* and the second sensor 519*b* are sensors having the same conditions but may sense whether contact with skin surface of the vagina 60 is made at positions different from each other. An optical sensor, a pressure sensor, or the like may be used as the first sensor 519*a* and the second sensor 519*b*.

The determination part 130 may receive sensed data that is sensed by the sensing device 519 and determine whether the third cartridge 510 is normally in contact or adhered to the inner wall of the vagina 60. For example, the determination part 130 may determine that the third cartridge 510 is normally adhered to the inner wall of the vagina 60 when both the first sensor 519*a* and the second sensor 519*b* are in contact with the inner wall of the vagina 60. Conversely, the determination part 130 may determine that the third cartridge 510 is abnormally in contact or adhered to the inner wall of the vagina when any one of the first sensor 519*a* and the second sensor 519*b* is not in contact with the inner wall of the vagina 60. The determined result may be displayed on the display 110 or the like to be recognized by an operator (not illustrated).

Also, the determination part 130 may control operation conditions of the third cartridge 510 on the basis of the sensed result of the sensing device 519. For example, the determination part 130 may control the ultrasound treatment part 514, the second driving device 418, and the like so that focused ultrasound is automatically irradiated when both the first sensor 519*a* and the second sensor 519*b* are in contact with the inner wall of the vagina 60. Also, the determination part 130 may control the third cartridge 510 to prevent focused ultrasound from being irradiated from the ultrasound treatment part 514 and prevent the thermal focal points 22 from being formed on places other than preset skin tissue when any one of the first sensor 519*a* and the second sensor 519*b* is not in contact with the inner wall of the vagina 60.

Here, the first sensor 519*a* and the second sensor 519*b* are preferably arranged on a virtual line 80 crossing the center of the window 512*a*. That is, as described above, because the focused ultrasound is irradiated through the window 512*a*, and whether the third cartridge 510 is normally placed is determined on the basis of a condition in which both the first sensor 519*a* and the second sensor 519*b* are sensed, whether the window 512*a* is in complete contact with the vagina 60 may be precisely determined by the first sensor 519*a* and the second sensor 519*b* disposed on the virtual line 80. When the first sensor 519*a* and the second sensor 519*b* are arranged by being deviated from the virtual line 80, precision in sensing whether the third cartridge 510 is normally placed inside the vagina 60 may be decreased.

To improve precision of determining whether the third cartridge 510 is normally placed, a plurality of sensors may be added in addition to the first sensor 519*a* and the second sensor 519b. Alternatively, the arrangement of the first sensor 519a and the second sensor 519b is not limited to the above, and the first sensor 519a and the second sensor 519b may be arranged in other various ways to determine whether the third cartridge 510 is normally placed. However, in consideration of the structure, the position during operation, etc. of the third cartridge 510, it may be important for the window 512a to be adhered to the inner wall of the vagina 60, and the sensing device 519 is preferably optimized to precisely sense whether the window 512a is adhered to the inner wall of the vagina 60.

The sensing device 519 and the determination part 130 sense an insertion depth of the third cartridge 510 into the vagina 60 and allow the operator to recognize the insertion depth. More specifically, the sensing device 519 may further include third sensors 519c arranged in a row along the longitudinal direction of the cartridge body 512. The third sensors 519c may be arranged by being spaced apart from each other at equal intervals on the same straight line crossing the longitudinal direction of the second cartridge body 512. The third sensors 519c may be spaced apart at specific units so that arrangement intervals of the third sensors 519c can be units for measuring the insertion depth of the third cartridge 510. The third sensors 519c may be implemented with optical sensors, pressure sensors, or the like having the same specifications. Accordingly, when the third cartridge 510 is inserted into the vagina 60, the third sensors 519cc sense contact by sequentially coming into contact with the vagina 60, and the determination part 130 may analyze sensed data transmitted from the third sensors 519c and display the insertion depth of the third cartridge 510 on the display 110 or the like to allow the operator to recognize the insertion depth.

The above-described focused ultrasound operation apparatus 10 according to an embodiment of the present invention may include the third cartridge 510 inserted into the vagina 60 of an operation target to irradiate the vagina 60 with focused ultrasound, the imaging probe 516 disposed in the third cartridge 510 to image skin tissue at a predetermined depth from skin surface of the vagina 60 to be treated, and the controller 130 configured to receive imaged data from the imaging probe 516 and control operation conditions of the ultrasound treatment part 514. In this case, the focused ultrasound operation apparatus 10 may allow the operator to check thickness, state, or the like of skin tissue to be treated, e.g., vaginal muscle, and control focused ultrasound irradiation conditions of the ultrasound treatment part 514 to be operation conditions suitable for the checked thickness, state, or the like. Accordingly, by imaging skin tissue inside the vagina on which a thermal focal point is to be formed during operation, and then comparing imaged data with reference data and changing irradiation conditions of the thermal focal point, the focused ultrasound operation apparatus according to the present invention may improve safety of gynecological disease treatment and/or vaginal tightening operation.

Also, the focused ultrasound operation apparatus 10 according to an embodiment of the present invention may include the third cartridge 510 inserted into the vagina 60 of an operation target to irradiate the vagina 60 with focused ultrasound, the sensing device 519 configured to sense whether the third cartridge 510 is in contact with skin tissue of the vagina 60, and the determination part 130 configured to receive sensed data of the sensing device 519, determine whether the third cartridge 510 is normally placed, and control movement of the third cartridge 510. In this case, the focused ultrasound operation apparatus 10 may determine whether the third cartridge 510 inserted into the vagina 60 is normally placed at a preset position during operation and precisely form the thermal focal points 22 on desired skin tissue. Accordingly, by determining whether a cartridge inserted into the vagina is normally placed inside the vagina during operation and then performing operation and precisely irradiating preset skin tissue with thermal focal points, the focused ultrasound operation apparatus according to the present invention may improve safety of gynecological disease treatment and vaginal tightening operation.

Also, in the focused ultrasound operation apparatus 10 according to an embodiment of the present invention, not only the operator can move the ultrasound treatment part 514 back and forth on the second operation handpiece 410, the operator can also rotate the ultrasound treatment part 514 by a predetermined angle in the range of 0° to 360° and form the thermal focal points 22 throughout inner wall of the vagina 60. In this case, because the operator can irradiate the entire inner wall of the vagina 60 with the thermal focal points 22 by simple manipulation of the second operation handpiece 410, operation time of gynecological disease treatment and/or vaginal tightening operation can be shortened, and operation efficiency can be improved. Accordingly, because the operator can form the thermal focal points throughout inner wall of the vagina while moving the ultrasound treatment part 514 back and forth and rotating the ultrasound treatment part 514 at the same time by simple manipulation of the operation handpiece, the focused ultrasound operation apparatus according to an embodiment of the present invention can shorten operation time of gynecological disease treatment and/or vaginal tightening operation and improve operation efficiency.

Also, the above-described focused ultrasound operation apparatus 10 according to an embodiment of the present invention may directly restore and regenerate the EPF 70 that is substantially responsible for vaginal contraction, instead of a surface of the vagina 60, by using focused ultrasound. In this case, because the focused ultrasound operation apparatus 10 causes less pain and no bleeding compared to the case of conventional $CO_2$ laser treatment equipment that directly irradiates the inner surface of the vagina 60 with laser and burns skin tissue to perform operation, there may be no inconvenience to daily life caused by pain and side effects that occur even after operation. Accordingly, due to being able to non-invasively regenerate or restore the EPF responsible for vaginal contraction by using focused ultrasound, the focused ultrasound operation apparatus for gynecological disease treatment and/or vaginal tightening operation according to the present invention may cause less pain and reduce bleeding compared to a laser apparatus that directly burns an inner wall of vagina and allow normal daily life even after operation.

Figure 12:
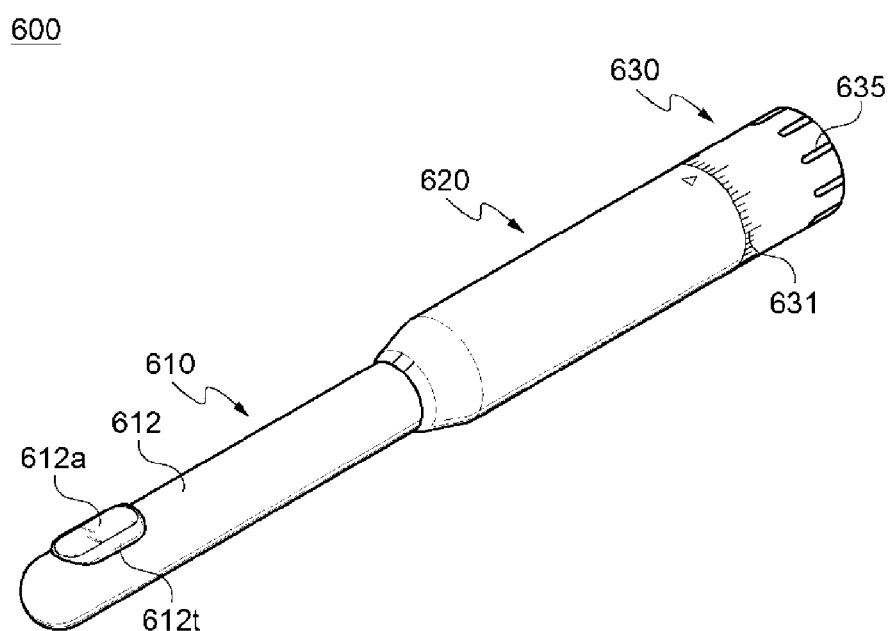
FIG. 12 is a perspective view schematically illustrating a focused ultrasound operation apparatus according to another embodiment of the present invention.
Figure 13:
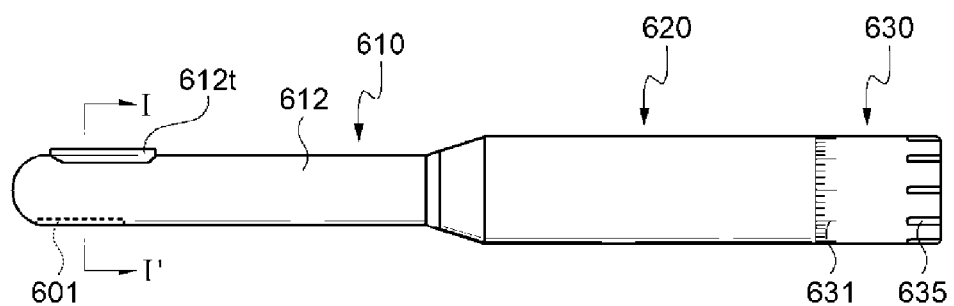
FIG. 13 is a side view of FIG. 12.
Figure 14:
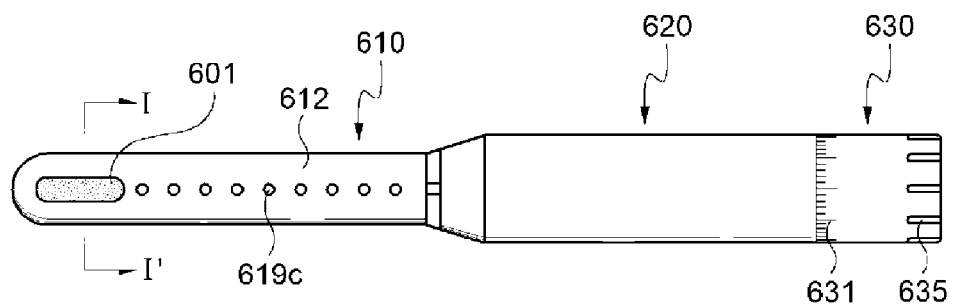
FIG. 14 is a bottom view of FIG. 12.
Figure 15:
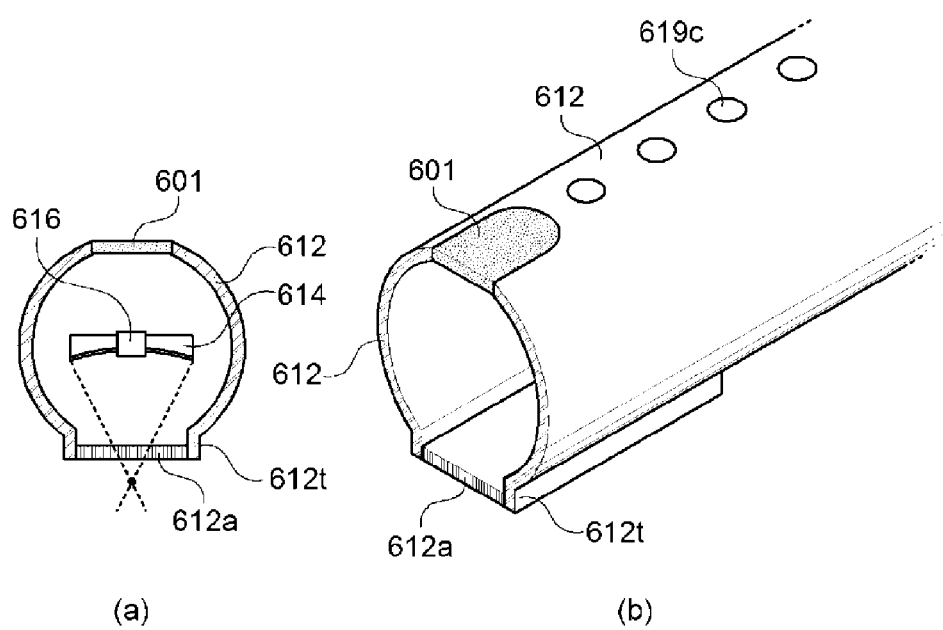
FIG. 15 is a view for describing the focused ultrasound operation apparatus illustrated in FIG. 12.

FIG. 12 is a perspective view schematically illustrating a focused ultrasound operation apparatus according to another embodiment of the present invention, FIG. 13 is a side view of FIG. 12, FIG. 14 is a bottom view of FIG. 12, and FIG. 15 is a view for describing the focused ultrasound operation apparatus illustrated in FIG. 12.

Referring to the drawings, a focused ultrasound operation apparatus according to another embodiment of the present invention may include a sixth cartridge 610 and a third operation handpiece and may further include a rotation controlling part.

Because the sixth cartridge 610 and the third operation handpiece may have shapes and structures similar to those of the third cartridge and the second operation handpiece described above with reference to FIGS. 7 to 11, overlapping description will be omitted below.

Although not illustrated, the focused ultrasound operation apparatus according to the present embodiment may be connected to the equipment main body 100 by a cable such as the above-described connecting cables 220 and 420. On the other hand, the focused ultrasound operation apparatus may solely operate without being connected to a cable or other equipment.

In one embodiment, the sixth cartridge 610 may include a sixth cartridge body 612, a window 612a, and a buffering part 601. The sixth cartridge body 612 may be formed in a cylindrical or bar shape. By the sixth cartridge body 612 being formed in the cylindrical or bar shape, the sixth cartridge 610 can be smoothly inserted into the human body and an unpleasant feeling may be minimized. Also, the sixth cartridge body 612 may be formed of a material having relatively high hardness. Accordingly, the sixth cartridge body 612 may be smoothly inserted into the human body and may be adhered to skin tissue and firmly supported while being inserted into the human body to protect parts disposed inside the sixth cartridge 610.

In one embodiment, the sixth cartridge body 612 may include the buffering part 601. Here, the buffering part 601 may be formed of a material having high flexibility compared to the sixth cartridge body 612 and serve to buffer a pressure change inside the sixth cartridge body 612. Also, the buffering part 601 may be formed of a material having elasticity in addition to flexibility. For example, the buffering part 601 is preferably formed with a material such as rubber or resin that has low elastic coefficient compared to hard resin. Particularly, because the buffering part 601 is formed of a material having relatively low elastic coefficient compared to that of the sixth cartridge body 612, an outer shape of the buffering part 601 may be relatively flexibly changed according to a pressure change inside the sixth cartridge body 612.

Also, a temperature of an ultrasound treatment part 614 increases as focused ultrasound irradiation operation proceeds, and a medium (319 etc. in FIG. 3) serves to cool the ultrasound treatment part 614 to prevent overheating thereof. In this process, the temperature of the medium increase. As a result, pressure inside the sixth cartridge body 612 increases, and such an increase in pressure may be decreased by having the buffering part 601.

Also, in a state in which the sixth cartridge body 612 is formed of a material having high hardness as described above, pressure distribution due to the medium may become uneven inside the sixth cartridge body 612 according to movement of the ultrasound treatment part 614, and as a result, excessive load may be acted on a specific area inside the sixth cartridge body 612. Moreover, because the ultrasound treatment part 614 moves inside the sixth cartridge body 612 in which various parts and the medium are filled in a relatively narrow space, the medium may act as resistance against movement of the ultrasound treatment part 614. However, because the buffering part 601 is disposed in the sixth cartridge body 612 in the focused ultrasound operation apparatus according to an embodiment of the present invention, the uneven pressure distribution inside the sixth cartridge body 612 may be mitigated and resistance against movement of the ultrasound treatment part 614 may also be decreased so that reliability of the cartridge is improved and service life of the cartridge is extended.

Also, when pressure inside the sixth cartridge body 612 increases, the increase in internal pressure may be mitigated as the buffering part 601 is relaxed. When the buffering part 601 remains relaxed even when the pressure inside the sixth cartridge body 612 is decreased, the degree in which the medium is filled inside the sixth cartridge body 612 may be decreased. That is, because volume inside the sixth cartridge body 612 increases due to relaxation of the buffering part 601, a situation in which the inside of the sixth cartridge body 612 is not completely filled with the medium may occur. Here, when an area between the ultrasound treatment part 614 and the window 612a is not completely filled with the medium, a problem may occur in ultrasound transmission. However, according to an embodiment of the present invention, because the buffering part 601 is formed of a material having elasticity in addition to flexibility, ultrasound may be stably transmitted while the pressure change inside the sixth cartridge body 612 is buffered.

In one embodiment, the buffering part 601 may be arranged at the opposite side of the window 612a. That is, the window 612a may be arranged in one direction (upward with reference to FIG. 13) from a side surface of the sixth cartridge body 612, and the buffering part 601 may be arranged in the other direction (downward with reference to FIG. 13) which is opposite to the above-described one direction from the side surface of the sixth cartridge body 612. Also, the buffering part 601 may be arranged by being deviated toward an end of the cartridge. For example, when a portion of the sixth cartridge 610 coupled to the third operation handpiece is viewed as one side of the sixth cartridge body 612, the buffering part 601 may be disposed at a position deviated toward one side or the other side of the sixth cartridge body 612 based on the longitudinal center of the sixth cartridge body 612. Furthermore, the outermost portion of the buffering part 601 may be arranged to be closer to the other side of the sixth cartridge body 612 than the outermost portion of the window 612a.

As described above, the pressure of the medium is unevenly change as the ultrasound treatment part 614 moves inside the sixth cartridge body 612 which is sealed. Particularly, at an end of the sixth cartridge body 612, i.e., an area close to one side or the other side of the sixth cartridge body 612, a pressure may be increased instantaneously due to movement of the ultrasound treatment part 614. Consequently, by arranging the buffering part 601 to be closer to one side or the other of the sixth cartridge body 612 than the center thereof, such an increase in pressure may be more effectively mitigated.

Also, an internal pressure change near the ultrasound treatment part 614 can be viewed as being relatively larger than an internal pressure change in other areas due to heat generation, movement, or the like of the ultrasound treatment part 614. Consequently, arranging the buffering part 601 in an area near the ultrasound treatment part 614 is advantageous in terms of mitigating the internal pressure change. However, because focused ultrasound irradiated from the ultrasound treatment part 614 is applied to skin tissue by passing through the above-described window 612a, when the window 612a is disposed at one surface of the sixth cartridge body 612, it is difficult for the buffering part 601 to be disposed at a position which is the same as or overlaps that of the window 612a.

By placing elements (see FIG. 19, etc.), such as the support, for driving the ultrasound treatment part 614 at the opposite side of the ultrasound treatment part 614, space arrangement efficiency may be improved even when space inside the cartridge is relatively narrow. However, the pressure distribution of the medium may become uneven also due to operation of the elements for driving the ultrasound treatment part 614. However, as in the embodiment of the present invention, by the buffering part 601 being arranged at the opposite side of the window 612*a*, the unevenness in pressure distribution may be more effectively mitigated.

In one embodiment, the sixth cartridge 610 may be realized so that a contact surface between the above-described window 612*a* and skin tissue is a flat surface. Furthermore, a protruding part 612*t* may be disposed on the sixth cartridge body 612, and the window 612*a* may be fixed by being coupled to an end of the protruding part 612*t*.

As described above, although insertion efficiency of the sixth cartridge 610 is improved by the sixth cartridge body 612 formed in the cylindrical or bar shape, when the window 612*a* disposed in the sixth cartridge body 612 is formed with a curvature similar to that of the sixth cartridge body 612, the possibility that the window 612*a* may not be able to be completely adhered to skin tissue is increased. On the other hand, when a skin contact surface of the window 612*a* is a flat surface as in the present embodiment, it is advantageous for the window 612*a* to be completely adhered to skin tissue.

Also, when the window 612*a* which is a flat surface is coupled to the sixth cartridge body 612 without change while the sixth cartridge body 612 is formed in the cylindrical shape, a distance from a central portion of the sixth cartridge body 612 to a central portion of the window 612*a* becomes smaller than a diameter of the sixth cartridge body 612. Consequently, the sixth cartridge body 612 may be more strongly adhered to skin tissue compared to a portion of the window 612*a*. That is, the degree to which the portion of the window 612*a* is adhered to the skin tissue may be decreased. However, according to an embodiment of the present invention, by the window 612*a* formed of a flat surface being fixed to one end of the a protruding part 612*t* protruding from the sixth cartridge body 612, the entire surface of the window 612*a* may be more tightly adhered to the skin tissue.

Although the buffering part 601, the window 612*a*, or the like have been described above with reference to FIGS. 12 to 15, similar principles may also be applied to other above-described embodiments. That is, as illustrated in FIG. 1, a buffering part 501 may also be disposed in the fifth cartridge 530 similarly formed as the third cartridge 510 and mitigate a problem caused by an increase in internal pressure. Also, a protruding part 512*t* and the window 512*a* described above may also be disposed in a seventh cartridge 540 illustrated in FIG. 1. Also, an example in which the buffering part 501 is disposed in the third cartridge 510 is illustrated in FIGS. 8 and 10.

In one embodiment, the above-described sixth cartridge 610 may be attached to and detached from one end of a third operation handpiece 620. Here, a rotation controlling part 630 may be disposed at the other end of the third operation handpiece 620, and the sixth cartridge 610 may be rotated by rotating the rotation controlling part 630 while gripping the third operation handpiece 620. Scales 631 may be disposed on a surface of the rotation controlling part 630 to allow the operator to more precisely recognize a degree of rotation of the cartridge. Also, to prevent the operator's hand from sliding from the rotation controlling part 630 in a process of rotating the rotation controlling part 630, a steel part 635 may be disposed.

Also, a fourth sensor 619*c* may be disposed at one surface of the sixth cartridge 610, and the function of the fourth sensor 619*c* is similar to that of the above-described third sensor 519*c*.

Figure 16:
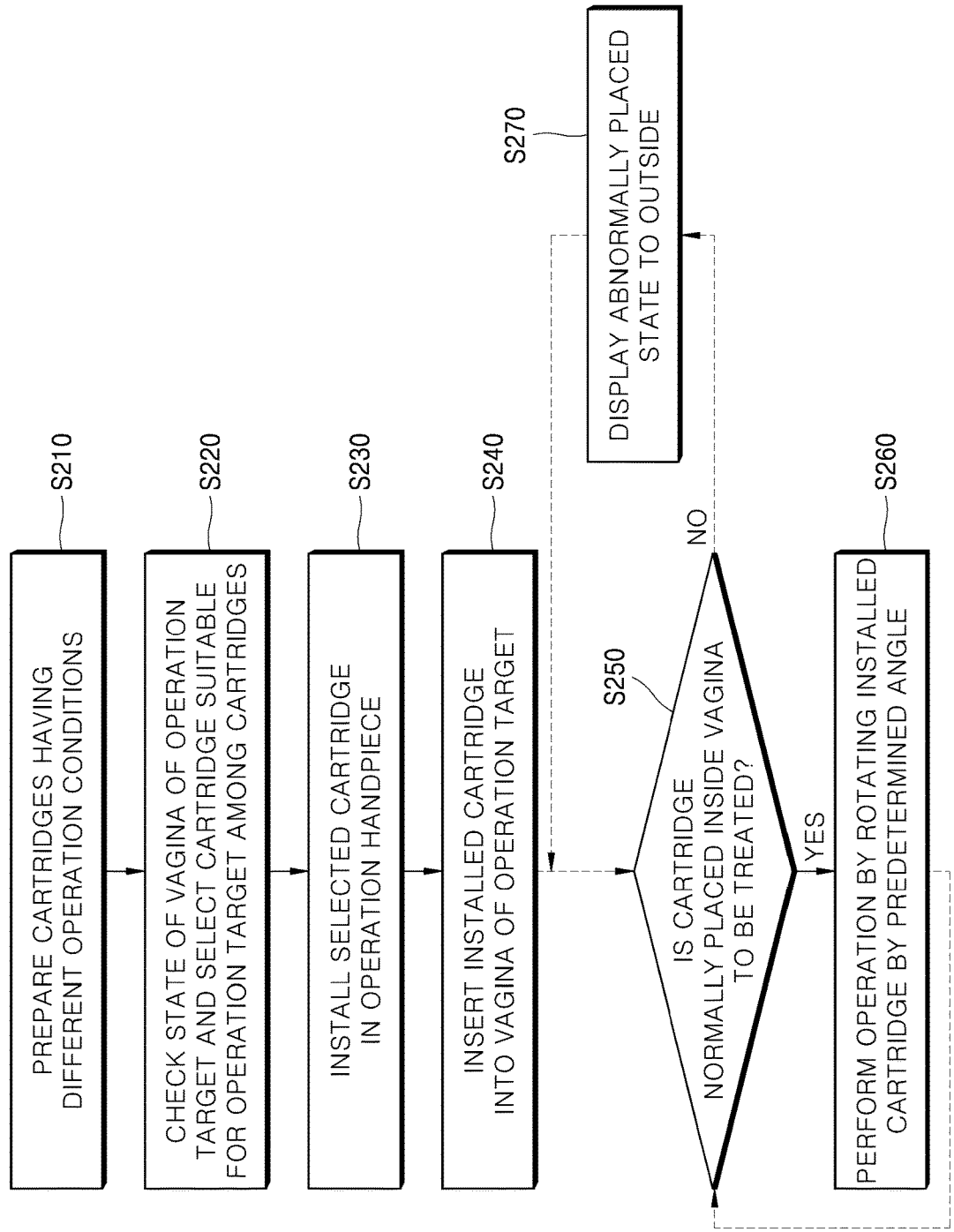
FIG. 16 is a flowchart for describing a process of gynecological disease and vaginal tightening operation according to an embodiment of the present invention.
Figure 17:
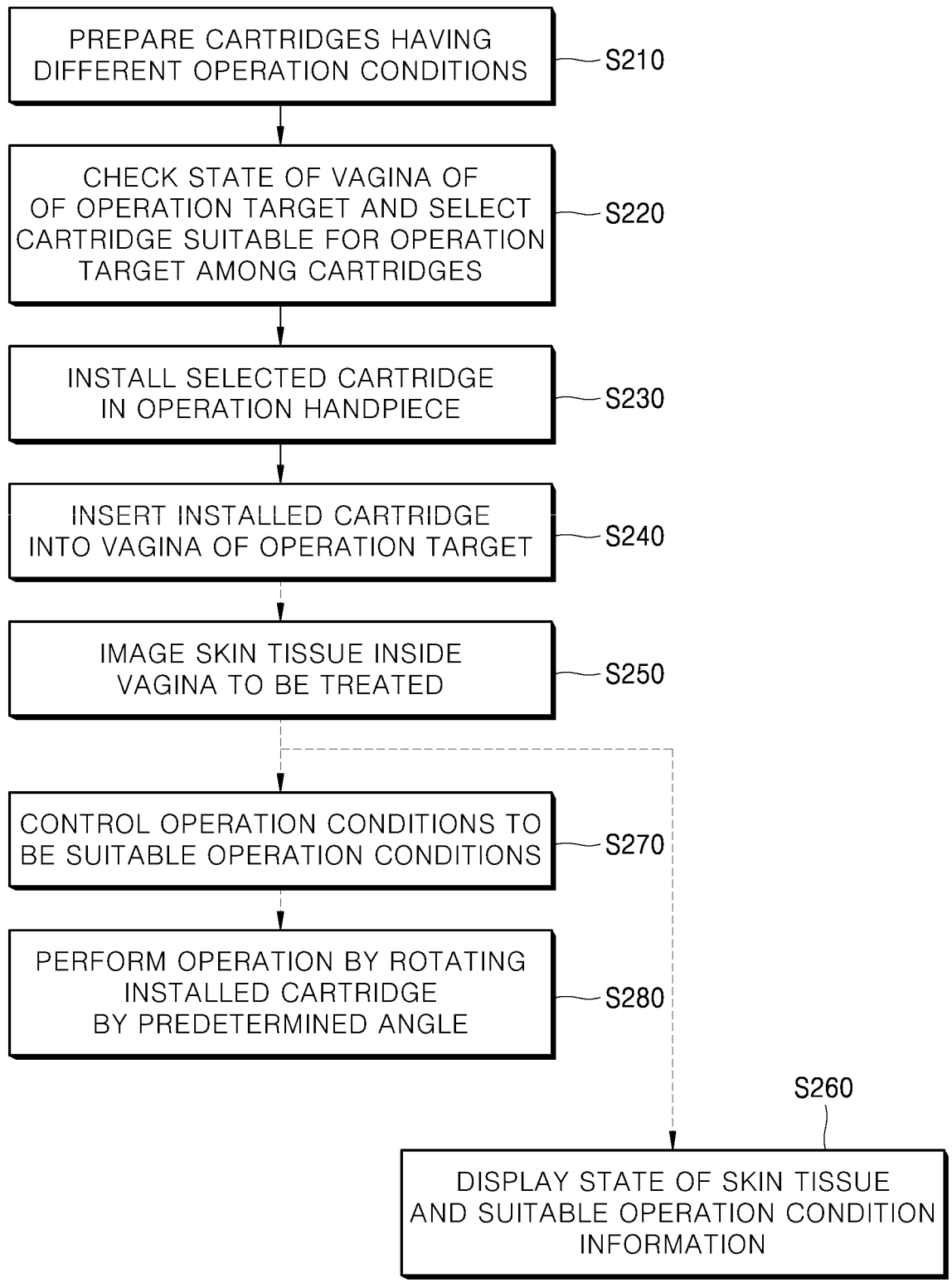
FIG. 17 is a flowchart for describing a process of gynecological disease and vaginal tightening operation according to another embodiment of the present invention.
Figure 18:
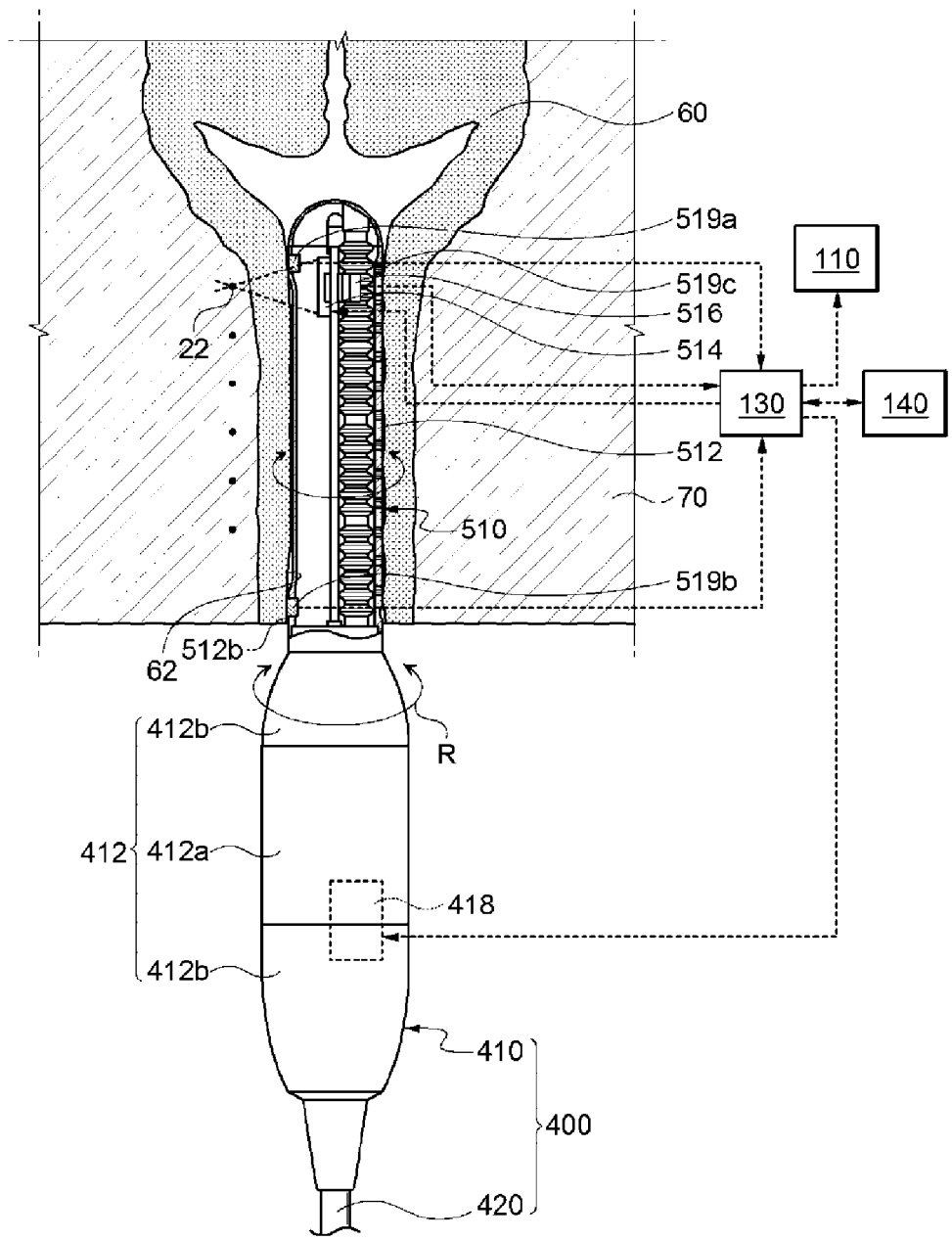
FIG. 18 is a view for describing a principle of performing operation using a focused ultrasound operation apparatus according to an embodiment of the present invention.
Figure 19:
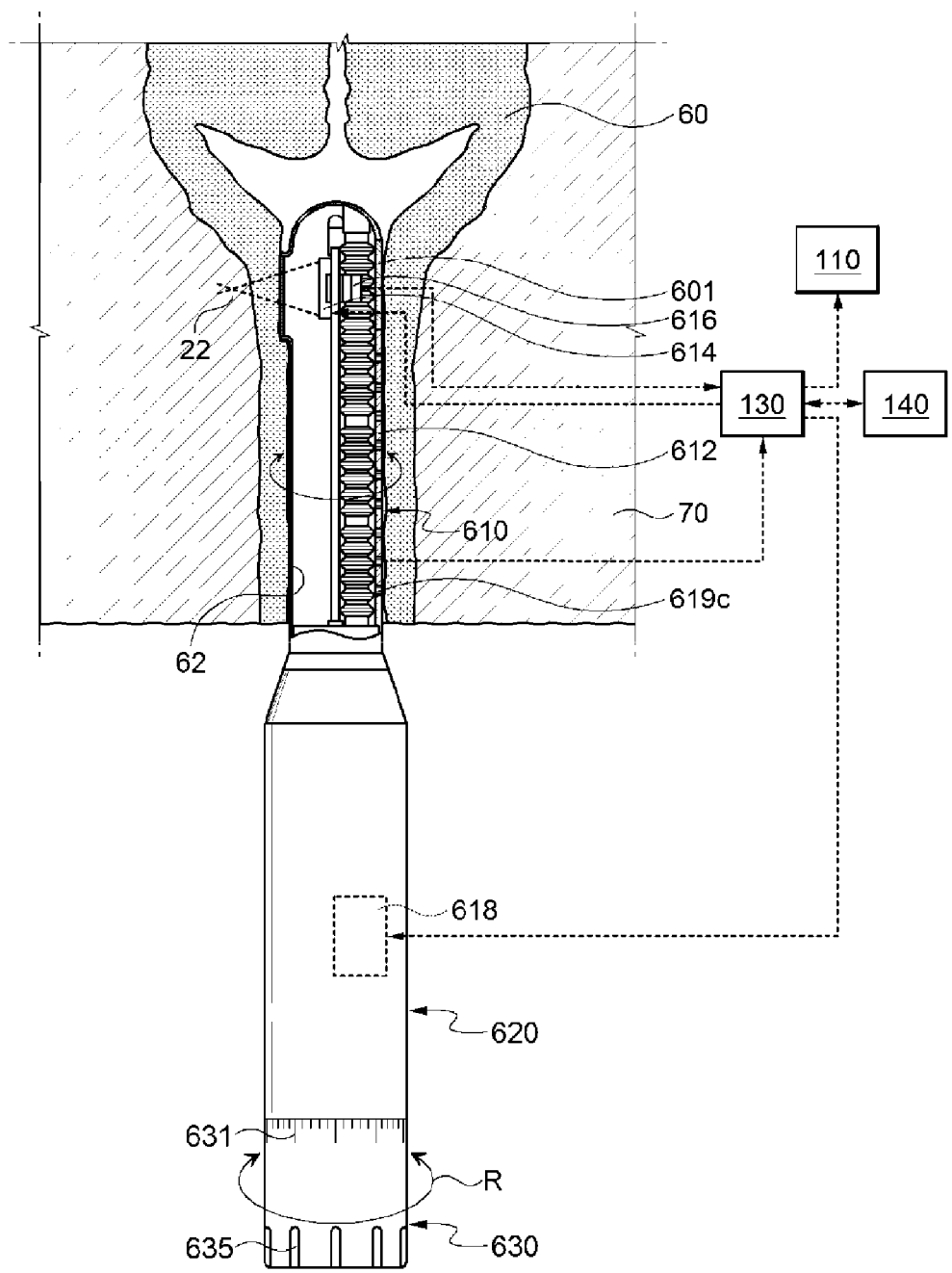
FIG. 19 is a view for describing a principle of performing operation using a focused ultrasound operation apparatus according to another embodiment of the present invention.

FIG. 16 is a flowchart for describing a process of gynecological disease and vaginal tightening operation according to an embodiment of the present invention, FIG. 17 is a flowchart for describing a process of gynecological disease and vaginal tightening operation according to another embodiment of the present invention, FIG. 18 is a view for describing a principle of performing operation using a focused ultrasound operation apparatus according to an embodiment of the present invention, and FIG. 19 is a view for describing a principle of performing operation using a focused ultrasound operation apparatus according to another embodiment of the present invention.

Referring to FIGS. 16 to 18, cartridges having different operation conditions may be prepared (S210). For example, the preparing of the cartridges may include preparing the third cartridge 510, the fourth cartridge 520, and the fifth cartridge 530 which have different focused ultrasound irradiation conditions. For example, the third cartridge 510, the fourth cartridge 520, and the fifth cartridge 530 may have different sizes of thermal focal points of focused ultrasound. In another example, the third cartridge 510, the fourth cartridge 520, and the fifth cartridge 530 may have different focused ultrasound irradiation depths, i.e., depths at which the thermal focal points are generated.

A cartridge suitable for an operation target may be selected among the cartridges by checking a state of vagina of the operation target (S220). For example, an operator (not illustrated) may figure out a state, a form, etc. of vagina of an operation target (not illustrated) and select a cartridge that is set to have suitable operation conditions among the third cartridge 510, the fourth cartridge 520, and the fifth cartridge 530. Here, the figuring out of the state of the operation target's vagina may be performed by the operator coupling any cartridge to the second operation handpiece 410 and then checking a state of skin tissue imaged by the second imaging probe 516 through the display 110.

When the operator has selected the third cartridge 510, the selected third cartridge (hereinafter, the selected cartridge 510) may be installed in the operation handpiece (S230). For example, the operator may install the selected cartridge 510 in the second operation handpiece 410. Here, the operator may insert the engaging part 512*c* of the selected cartridge 510 into the second guide part 416 of the second operation handpiece 410 to engage the selected cartridge 510 with the second operation handpiece 410.

Next, the installed cartridge 510 may be inserted into the vagina 60 of the operation target (S240). More specifically, the operator may insert the selected cartridge 510 into the vagina 60 by a desired depth. Here, for smooth insertion of the selected cartridge 510 and efficient ultrasound operation, an auxiliary substance such as ultrasound gel may be applied to the selected cartridge 510 and used.

Whether the selected cartridge 510 is normally placed inside the vagina 60 to be treated may be determined (S250). More specifically, the determination part 130 may receive sensed data from the first sensor 519*a* and the second sensor 519*b* and determine whether the both the first sensor 519*a* and the second sensor 519*b* are sensed as being in normal contact with skin surface of the vagina 60. In this case, the determination part 130 may determine that the selected cartridge 510 is normally placed inside the vagina 60. Conversely, the determination part 130 may receive sensed data from the first sensor 519*a* and the second sensor 519*b* and determine that the selected cartridge 510 is abnormally placed inside the vagina 60 when any one of the first sensor 519*a* and the second sensor 519*b* is checked as not being in contact with skin surface of the vagina 60. The determination part 130 may sense sensed data transmitted from a sensor that has sensed contact with the inner wall of the vagina 60 among the third sensors 519*c* as the selected cartridge 510 is inserted into the vagina 60 and may measure the insertion depth of the selected cartridge 510. By pieces of information measured by the first sensor 519a, the second sensor 519b, and the third sensors 519c as described above being gathered, determination related to whether the selected cartridge 510 is normally placed may be performed. Accordingly, the determination part 130 may display a state in which the cartridge 510 is abnormally placed through a display means such as the display 110 to allow the operator to recognize the state (S270).

Also, when the selected cartridge 510 is normally placed inside the vagina 60, gynecological disease treatment and vaginal tightening operation may be performed by rotating the installed cartridge 510 by a predetermined angle (S260). For example, when the position of the second operation handpiece 410 is decided, the operator may appropriately manipulate the manipulation part 120, a second operation switch 414, and the like to allow the thermal focal point 22 of focused ultrasound to be formed at a set position on skin tissue inside the vagina 60 by the ultrasound treatment part 514. Here, as the selected cartridge 510 is linearly reciprocated and rotated by the second driving device 418, manual manipulation of the operator, or the like, the plurality of thermal focal points 22 may be three-dimensionally formed along the inner circumference of the vagina 60.

More specifically, the operator may hold and fix the fixing part 412a of the second operation handpiece 410 with one hand and then turn an operation switch (not illustrated) disposed in the second operation handpiece 410 on or off or operate a foot switch with the other hand. Accordingly, the ultrasound treatment part 514 inside the selected cartridge 510 may move back and forth along the longitudinal direction of the selected cartridge 510 and form the thermal focal points 22 along a first virtual line on skin tissue at the inner wall of the vagina. When forming the thermal focal points 22 by the above-described back and forth movement is finished, the operator may rotate the cartridge rotating part 412b of the second operation handpiece 410 by a predetermined angle with the other hand. The selected cartridge 510 may rotate by a predetermined angle along a rotating direction R based on the central axis of the selected cartridge 510 according to rotation of the cartridge rotating part 412b. Also, the operator may operate the operation switch or the foot switch so that the ultrasound treatment part 514 forms the thermal focal points 22 along a second line which is parallel with the first line and is spaced a predetermined distance from the first line.

By repeating the above-described procedure, the thermal focal points 22 may be formed throughout skin tissue inside the vagina 60 as a plurality of dots spaced apart from each other along the same line at a predetermined depth. Accordingly, specific skin tissue inside the vagina 60 is appropriately damaged and stimulated by the thermal focal points 22, and damaged skin tissue is restored and regenerated so that the skin tissue of the vagina 60 can be regenerated or the EPF 70 can be densified.

As described above, in a focused ultrasound operation method according to an embodiment of the present invention, whether the third cartridge 510 inserted into the vagina 60 to irradiate the vagina 60 with focused ultrasound is normally adhered to skin tissue of the vagina 60 is determined, and the third cartridge 510 may be allowed to operate only when the third cartridge 510 is normally placed. In this case, because whether the third cartridge 510 inserted into the vagina 60 is normally placed at a preset position during operation can be determined and the thermal focal points 22 can be precisely formed on desired skin tissue, the focused ultrasound operation method can prevent the thermal focal points 22 from being formed on places other than preset skin tissue. Accordingly, by determining whether a cartridge inserted into vagina is normally placed inside the vagina during operation and then performing operation to allow preset skin tissue to be precisely irradiated with thermal focal points, the focused ultrasound operation method according to the present invention may improve safety of gynecological disease treatment and vaginal tightening operation.

Referring to FIGS. 17 and 18, cartridges having different operation conditions may be prepared (S210). For example, the preparing of the cartridges may include preparing the third cartridge 510, the fourth cartridge 520, and the fifth cartridge 530 which have different focused ultrasound irradiation conditions. For example, the third cartridge 510, the fourth cartridge 520, and the fifth cartridge 530 may have different sizes of thermal focal points of focused ultrasound. In another example, the third cartridge 510, the fourth cartridge 520, and the fifth cartridge 530 may have different focused ultrasound irradiation depths, i.e., depths at which the thermal focal points are generated.

A cartridge suitable for an operation target may be selected among the cartridges by checking a state of vagina of the operation target (S220). For example, an operator (not illustrated) may figure out a state, a form, etc. of vagina of an operation target (not illustrated) and select a cartridge that is set to have suitable operation conditions among the third cartridge 510, the fourth cartridge 520, and the fifth cartridge 530. Here, the figuring out of the state of the operation target's vagina may be performed by the operator coupling any cartridge to the second operation handpiece 410 and then checking a state of skin tissue imaged by the second imaging probe 516 through the display 110.

When the operator has selected the third cartridge 510, the selected third cartridge (hereinafter, the selected cartridge 510) may be installed in the operation handpiece (S230). For example, the operator may install the selected cartridge 510 in the second operation handpiece 410. Here, the operator may insert the engaging part 512c of the selected cartridge 510 into the second guide part 416 of the second operation handpiece 410 to engage the selected cartridge 510 with the second operation handpiece 410.

Next, the installed cartridge 510 may be inserted into the vagina 60 of the operation target (S240). More specifically, the operator may insert the selected cartridge 510 into the vagina 60 by a desired depth. Here, for smooth insertion of the selected cartridge 510 and efficient ultrasound operation, an auxiliary substance such as ultrasound gel may be applied to the selected cartridge 510 and used.

When the selected cartridge 510 is normally inserted into the vagina 60, skin tissue inside the vagina 60 to be treated may be imaged (S250). More specifically, the second imaging probe 516 disposed inside the cartridge 510 inserted into the vagina 60 may irradiate imaging ultrasound toward skin tissue inside the vagina 60 which is irradiated with the focused ultrasound. The imaging ultrasound may be transmitted through the window 512a disposed in the cartridge 510. The imaged data by the imaging probe 516 may be transmitted to the controller 130, and a state of skin tissue and operation condition information and the like suitable for the state may be displayed so that the operator can recognize the skin tissue inside the vagina 60 (S260). The displaying of the information may be guided to the operator by the display 110.

Operation conditions may be controlled to be suitable operation conditions (S270). For example, the controller 130 may compare the imaged data with the reference data and figure out whether a position of muscle of the vagina 60 or whether the thickness of muscle of the vagina 60 is larger or smaller than a preset thickness. When the thickness of muscle of the vagina 60 is larger than a vertical width of the thermal focal point 22, the controller 130 may control the ultrasound treatment part 514 so that the vertical width of the thermal focal point 22 becomes smaller than the thickness of muscle of the vagina 60 to prevent the thermal focal point 22 from being formed on tissue other than muscle of the vagina 60. Alternatively, when the thickness of muscle of the vagina 60 is smaller than a specific thickness, the controller 130 may control the ultrasound treatment part 514 so that the irradiation intensity or strength of the focused ultrasound is decreased to prevent damage to the muscle of the vagina 60. Moreover, the controller 130 may control the second driving device 418 so that a position of the ultrasound treatment part 514 is aligned to allow the thermal focal point 22 to be precisely formed on skin tissue to be treated. For the controlling of the operation conditions as described above, the controller 130 may compare the imaged data with the reference data in the database 140 and allow the ultrasound treatment part 514 or the second driving device 418 to be automatically controlled. Alternatively, the controller 130 may display a precise image on the display 110 and guide suitable operation conditions, changing the operation conditions may be performed by the operator manipulating the manipulation part 120 and controlling conditions of the ultrasound treatment part 514 or the second driving device 418.

Also, when the operation conditions are controlled, gynecological disease treatment and/or vaginal tightening operation may be performed by rotating the installed cartridge 510 by a predetermined angle (S280). For example, when the position of the second operation handpiece 410 is decided, the operator may appropriately manipulate the manipulation part 120, the second operation switch 414, and the like to allow the thermal focal point 22 of focused ultrasound to be formed at a set position on skin tissue inside the vagina 60 by the ultrasound treatment part 514. Here, as the selected cartridge 510 is linearly reciprocated and rotated by the second driving device 418, manual manipulation of the operator, or the like, the plurality of thermal focal points 22 may be three-dimensionally formed along the inner circumference of the vagina 60.

More specifically, the operator may hold and fix the fixing part 412*a* of the second operation handpiece 410 with one hand and then turn an operation switch (not illustrated) disposed in the second operation handpiece 410 on or off or operate a foot switch with the other hand. Accordingly, the ultrasound treatment part 514 inside the selected cartridge 510 may move back and forth along the longitudinal direction of the selected cartridge 510 and form the thermal focal points 22 along the first virtual line on skin tissue at the inner wall of the vagina. When forming the thermal focal points 22 by the above-described back and forth movement is finished, the operator may rotate the cartridge rotating part 412*b* of the second operation handpiece 410 with the other hand. The selected cartridge 510 may rotate by a predetermined angle along the rotating direction R based on the central axis of the selected cartridge 510 according to rotation of the cartridge rotating part 412*b*. Also, the operator may operate the operation switch or the foot switch so that the ultrasound treatment part 514 forms the thermal focal points 22 along the second line which is parallel with the first line and is spaced a predetermined distance from the first line.

By repeating the above-described procedure, the thermal focal points 22 may be formed throughout skin tissue inside the vagina 60 as a plurality of dots spaced apart from each other along the same line at a predetermined depth. Accordingly, specific skin tissue inside the vagina 60 is appropriately damaged and stimulated by the thermal focal points 22, and damaged skin tissue is restored and regenerated so that the skin tissue of the vagina 60 can be regenerated or the EPF 70 can be densified.

Before the performing of the gynecological disease treatment and/or vaginal tightening operation (S280), determining whether the selected cartridge 510 is normally placed at the inner wall of the vagina 60 to be treated may be added. More specifically, the determination part 130 may receive sensed data from the first sensor 519*a* and the second sensor 519*b* and determine whether both the first sensor 519*a* and the second sensor 519*b* are sensed as normally being in contact with skin surface of the vagina 60. In this case, the determination part 130 may determine that the selected cartridge 510 is normally placed inside the vagina 60. Conversely, the determination part 130 may receive sensed data from the first sensor 519*a* and the second sensor 519*b* and determine that the selected cartridge 510 is abnormally placed inside the vagina 60 when any one of the first sensor 519*a* and the second sensor 519*b* is checked as not being in contact with skin surface of the vagina 60. The determination part 130 may sense sensed data transmitted from a sensor that has sensed contact with the inner wall of the vagina 60 among the third sensors 519*c* as the selected cartridge 510 is inserted into the vagina 60 and may measure the insertion depth of the selected cartridge 510. By pieces of information measured by the first sensor 519*a*, the second sensor 519*b*, and the third sensors 519*c* as described above being gathered, determination related to whether the selected cartridge 510 is normally placed may be performed. Accordingly, the determination part 130 may display a state in which the cartridge 510 is abnormally placed through a display means such as the display 110 to allow the operator to recognize the state. As described above, when the selected cartridge 510 is normally placed inside the vagina 60, gynecological disease treatment and vaginal tightening operation may be performed.

The above-described focused ultrasound operation method according to an embodiment of the present invention may allow the operator to check thickness, state, or the like of skin tissue to be treated, e.g., vaginal muscle, and control focused ultrasound irradiation conditions to be operation conditions suitable for the checked thickness, state, or the like. Accordingly, by comparing imaged data of skin tissue inside the vagina on which a thermal focal point is to be formed during operation with reference data and changing focused ultrasound operation conditions to be suitable operation conditions, the focused ultrasound operation method according to the present invention may improve safety of gynecological disease treatment and/or vaginal tightening operation.

Also, the focused ultrasound operation method according to an embodiment of the present invention may allow a state of an operation target to be figured out, the cartridge 510 having desired operation conditions to be selected from the second cartridge set 500, and the selected cartridge 510 to be installed in the second operation handpiece 410 to perform operation. Accordingly, due to being able to prepare cartridges having operation conditions suitable for the state of vagina of the operation target to be compatible with an operation handpiece and then install a selected cartridge in the operation handpiece to perform operation, the focused ultrasound operation method according to an embodiment of the present invention may perform patient-tailored operation using single piece of equipment by replacing a cartridge.

An example in which operation is performed by coupling the sixth cartridge 610 according to an embodiment that has been described with reference to FIGS. 12 to 15 to the third operation handpiece 620 is illustrated in FIG. 19, and description overlapping with the above description will be omitted.

When the sixth cartridge 610 is inserted into the vagina 60, the window is adhered to skin tissue. The ultrasound treatment part 614 operates in this state and forms the thermal focal point 22. Also, a third driving device 618 that operates in a similar way as the above-described second driving device 418 may be disposed in the third operation handpiece 620 and linearly move the ultrasound treatment part 614. Here, an increase in internal pressure caused by operation, movement, or the like of the ultrasound treatment part 614 may be mitigated by the buffering part 601. Also, the sixth cartridge 610 may be rotated by rotating the rotation controlling part 630 while gripping the third operation handpiece 620. A third imaging probe 616 and the like may be disposed in the ultrasound treatment part 614 to allow required information such as information on an inside of skin tissue to be collected and provided.

As described above, in the focused ultrasound operation method according to an embodiment of the present invention, an operator may evenly form the thermal focal points 22 throughout the inner wall of the vagina 60 by moving the ultrasound treatment part 514 in the cartridge installed in the second operation handpiece 410 back and forth and rotating the ultrasound treatment part 514 by a predetermined angle just by simple manipulation. Accordingly, because an operator can form the thermal focal points throughout the inner wall of the vagina while moving the ultrasound treatment part back and forth and rotating the ultrasound treatment part at the same time by simple manipulation of the operation handpiece, the focused ultrasound operation method according to an embodiment of the present invention can shorten operation time of gynecological disease treatment and/or vaginal tightening operation and improve operation efficiency.

Also, in the above-described focused ultrasound operation method according to an embodiment of the present invention, EPF 70 that is substantially responsible for vaginal contraction may be directly restored and regenerated instead of a surface of the vagina 60 by using focused ultrasound. Accordingly, due to being able to non-invasively regenerate or restore the EPF responsible for vaginal contraction by using focused ultrasound, the focused ultrasound operation method according to the present invention may cause less pain and no bleeding compared to a laser apparatus that directly burns an inner wall of vagina and allow normal daily life even after operation.

<Description of reference numerals>

10, 600: Focused ultrasound operation apparatus
12, 22, 30, 50: Thermal focal point    20: Subcutaneous fat
40: Skin tissue which is operation target
60: Vagina                              70: EPF
80: Virtual line                        100: Equipment main body
110: Display                            120: Manipulation part
130: Controller                         140: Database
200: First handpiece assembly
210: First operation handpiece          212: First handle part
212a: First operation switch            214: First guide part <Description of reference numerals>

216: First imaging probe                218: First driving device
220: First connecting cable             300: First cartridge set
310: First cartridge                    312: First cartridge body
314: Treatment transducer               316: Support
320: Second cartridge                   400: Second handpiece assembly
410: Second operation handpiece         412: Second handle part
414: Second operation switch            416: Second guide part
418: Second driving device              420: Second connecting cable
500: Second cartridge set
510: Third cartridge                    512: Second cartridge body
514: Ultrasound treatment part          516: Second imaging probe
519: Sensing device                     520: Fourth cartridge
530: Fifth cartridge                    540: Seventh cartridge
601: Buffering part                     610: Sixth cartridge
612: Sixth cartridge body               612a: Window
612t: A protruding part                 614: Ultrasound treatment part
616: Third imaging probe                618: Third driving device
619c: Fourth sensor                     620: Third operation handpiece
630: Rotation controlling part          631: Scales   635: Steel part Due to being able to be utilized in various types of operation including obesity treatment, skin care, and gynecological disease treatment, a focused ultrasound operation apparatus according to an embodiment of the present invention can be used in the medical industry and the beauty industry.

The invention claimed is:

1. A focused ultrasound operation apparatus comprising:
an operation handpiece configured to be used as a handle for an operator;
a cartridge insertable into a vagina of an operation target, the cartridge configured to be attachable to and detachable from the operation handpiece and having an ultrasound treatment part configured to generate focused ultrasound disposed therein;
a driving device configured to drive the ultrasound treatment part so that the ultrasound treatment part is configured to move back and forth along a longitudinal direction of the cartridge;
a sensing device configured to determine whether the cartridge is normally placed inside the vagina; and
a determination part configured to review sensed data sent from the sensing device and determine whether the cartridge is normally placed inside the vagina,
wherein the cartridge includes:
  a cartridge body; and
  a window provided at a circumference of the cartridge body in the longitudinal direction of the cartridge so that the focused ultrasound generated from the ultrasound treatment part is transmitted to outside, and
wherein the sensing device includes:
  a first sensor arranged at one side of the window and configured to sense a contact with a first position in the vagina; and
  a second sensor arranged at another side of the window and configured to sense a contact with a second position in the vagina which is different from the first position, and
wherein the determination part is configured to determine that the cartridge is normally placed inside the vagina when both the first sensor and the second sensor are sensed as being in contact with a skin surface inside the vagina, and configured to determine that the cartridge is abnormally placed when at least one of the first sensor or the second sensor is not sensed as being in contact with the skin surface inside the vagina.

2. The focused ultrasound operation apparatus of claim 1, wherein the sensing device includes third sensors arranged to be spaced apart from each other along the longitudinal direction of the cartridge; and
the determination part is configured to receive sensed data from the third sensors and to calculate a depth by which the cartridge is inserted into the vagina during operation.

3. The focused ultrasound operation apparatus of claim 1, further comprising:
an imaging probe configured to image a skin tissue at a predetermined depth from a skin surface of the vagina; and
a controller configured to analyze imaged data received from the imaging probe and to control irradiation conditions of the focused ultrasound.

4. A focused ultrasound operation apparatus comprising:
an operation handpiece that is used as a handle;
a cartridge that is insertable into a vagina of an operation target, is attachable to and detachable from the operation handpiece, and has an ultrasound treatment part configured to generate focused ultrasound disposed therein;
a driving device configured to drive the ultrasound treatment part so that the ultrasound treatment part moves back and forth along a longitudinal direction of the cartridge;
an imaging probe configured to image a skin tissue at a predetermined depth from a skin surface of the vagina; and
a controller configured to analyze imaged data received from the imaging probe and to control irradiation conditions of the focused ultrasound,
wherein the controller is configured to compare the imaged data measured by the imaging probe with preset reference data, and when a thickness of muscle of the vagina is deviated from a preset thickness of vagina, the controller is configured to control the ultrasound treatment part so that irradiation of the focused ultrasound from the ultrasound treatment part is inhibited.

5. The focused ultrasound operation apparatus of claim 4, wherein the imaging probe is configured to image a skin tissue at a depth in a range of approximately 0.5 mm to 3.0 mm from a surface of the vagina, and the controller is configured to control the irradiation conditions of the focused ultrasound of the ultrasound treatment part based on the skin tissue measured by the imaging probe.

6. The focused ultrasound operation apparatus of claim 4, wherein the imaging probe is configured to image the thickness of muscle of the vagina, and the controller is configured to control irradiation conditions of the focused ultrasound of the ultrasound treatment part based on the thickness of muscle of the vagina measured by the imaging probe.

7. The focused ultrasound operation apparatus of claim 4, wherein the imaging probe is coupled to the ultrasound treatment part and is configured to move back and forth together with the ultrasound treatment part.

8. The focused ultrasound operation apparatus of claim 4, wherein the cartridge includes:
a cartridge body; and
a window provided at a circumference of the cartridge body in the longitudinal direction of the cartridge so that the focused ultrasound generated from the ultrasound treatment part is transmitted to outside, and
the imaging probe is configured to image the thickness of muscle of the vagina by irradiating the vagina with ultrasound through the window.

9. The focused ultrasound operation apparatus of claim 4, wherein
the operation handpiece includes a cartridge rotating part configured to rotate the cartridge about a central axis of the cartridge,
the cartridge rotating part is coupled to the cartridge and configured to rotate together with the cartridge, and
the operation handpiece includes a fixing part to which the cartridge rotating part is rotatably coupled.

10. The focused ultrasound operation apparatus of claim 4, wherein the controller is configured to control an irradiation depth of the focused ultrasound of the ultrasound treatment part so that a thermal focal point that is formed of the focused ultrasound is formed within a vertical width of the thickness of muscle of the vagina.

11. A focused ultrasound operation apparatus comprising:
an operation handpiece including a handle part that is used as a handle for an operator;
a cartridge having an ultrasound treatment part configured to generate high intensity focused ultrasound (HIFU) disposed therein; and
a driving device configured to drive the ultrasound treatment part,
wherein the cartridge includes:
a cartridge body configured to be attached to or detached from the operation handpiece, the cartridge body having a cylindrical shape to be insertable into a vagina of an operation target; and
a window coupled to a side surface of the cartridge body and configured to transmit the HIFU,
wherein a skin contact surface of the window has a flat surface, and
wherein the cartridge body includes a protruding part configured to protrude in a direction perpendicular to a longitudinal direction of the cartridge body from the side surface of the cartridge body, and has the window coupled thereto.

12. The focused ultrasound operation apparatus of claim 11, wherein a surface including a boundary line between the protruding part and the cartridge body is a curved surface, and a surface including a line of contact between the protruding part and the window is a flat surface.

* * * * *